US009474835B2

(12) United States Patent
Haraguchi et al.

(10) Patent No.: US 9,474,835 B2
(45) Date of Patent: Oct. 25, 2016

(54) BLOCK COPOLYMER AND ANTITHROMBOTIC COATING AGENT

(75) Inventors: Kazutoshi Haraguchi, Chiba (JP); Kazuomi Kubota, Sakura (JP); Tooru Takehisa, Chiba (JP); Tetsuo Takada, Sakura (JP); Noriko Santou, Sakura (JP)

(73) Assignees: Kawamura Institute of Chemical Research, Sakura-shi (JP); DIC Corporation, Tokyo (JP)

( * ) Notice: Subject to any disclaimer, the term of this patent is extended or adjusted under 35 U.S.C. 154(b) by 0 days.

(21) Appl. No.: 14/237,664

(22) PCT Filed: Aug. 10, 2012

(86) PCT No.: PCT/JP2012/070487
§ 371 (c)(1),
(2), (4) Date: Apr. 11, 2014

(87) PCT Pub. No.: WO2013/024815
PCT Pub. Date: Feb. 21, 2013

(65) Prior Publication Data
US 2014/0235748 A1    Aug. 21, 2014

(30) Foreign Application Priority Data

Aug. 15, 2011   (JP) .................. 2011-177589

(51) Int. Cl.
| C08F 220/56 | (2006.01) |
| C08F 220/58 | (2006.01) |
| C09D 133/26 | (2006.01) |
| C09D 153/00 | (2006.01) |
| A61L 33/06 | (2006.01) |
| C08F 293/00 | (2006.01) |

(52) U.S. Cl.
CPC ............. *A61L 33/064* (2013.01); *A61L 33/06* (2013.01); *C08F 220/56* (2013.01); *C08F 293/005* (2013.01); *C09D 133/26* (2013.01); *C09D 153/00* (2013.01); *C08F 2438/03* (2013.01)

(58) Field of Classification Search
None
See application file for complete search history.

(56) References Cited

U.S. PATENT DOCUMENTS

| 6,518,343 | B1 * | 2/2003 | Lucast | .................. C09J 133/08 424/448 |
| 6,663,855 | B2 * | 12/2003 | Frechet | .................. A61K 8/90 424/401 |
| 2002/0098214 | A1 * | 7/2002 | Adams | .................. A61K 8/898 424/401 |
| 2002/0159965 | A1 * | 10/2002 | Frechet | .................. A61K 8/90 424/70.16 |
| 2003/0130160 | A1 * | 7/2003 | Eason | .................. C08L 53/00 510/475 |
| 2003/0191044 | A1 * | 10/2003 | Carswell | .................. C11D 3/046 510/476 |
| 2003/0195136 | A1 * | 10/2003 | Carswell | .................. C08F 293/005 510/475 |
| 2009/0143545 | A1 * | 6/2009 | Guerret | .................. C08L 75/04 525/92 C |
| 2014/0235748 | A1 * | 8/2014 | Haraguchi | .................. A61L 33/064 523/112 |

FOREIGN PATENT DOCUMENTS

| CN | 101094698 A | 12/2007 |
| CN | 101663340 A | 3/2010 |
| CN | 101977638 A | 2/2011 |
| EP | 1156067 A2 | 11/2001 |
| JP | 04-152952 A | 5/1992 |
| JP | 09-023876 A | 1/1997 |
| JP | 10-251609 A | 9/1998 |
| JP | 2806510 B2 | 9/1998 |
| JP | 11-287802 A | 10/1999 |
| JP | 2002-105136 A | 4/2002 |
| JP | 3459836 B2 | 10/2003 |
| JP | 2004-510719 A | 4/2004 |
| JP | 2004-269676 A | 9/2004 |
| JP | 2004-339165 A | 12/2004 |
| JP | 2006-131823 A | 5/2006 |
| JP | 2007-146133 A | 6/2007 |
| JP | 2007-289299 A | 11/2007 |
| JP | 2008-194363 A | 8/2008 |
| JP | 2008-220786 A | 9/2008 |
| JP | 4162028 B2 | 10/2008 |
| JP | 2008-264266 A | 11/2008 |
| JP | 2008-289864 A | 12/2008 |
| JP | 4317183 B2 | 8/2009 |
| JP | 4404445 B2 | 1/2010 |
| JP | 2011-006555 A | 1/2011 |
| JP | 4746984 B2 | 8/2011 |
| JP | 2012-165730 A | 9/2012 |
| JP | 2013-057058 A | 3/2013 |
| WO | WO-02/28358 A1 | 4/2002 |
| WO | WO-2004/087228 A1 | 10/2004 |

OTHER PUBLICATIONS

Office Action mailed Feb. 4, 2015, issued for the Chinese patent application No. 201280039648.9 and English translation thereof.
(Continued)

Primary Examiner — Peter A Salamon
(74) Attorney, Agent, or Firm — Locke Lord LLP

(57) ABSTRACT

The object of the present invention is achieved by providing a copolymer, in particular, a block copolymer which has excellent coating formation ability, adhesive properties to a substrate, and does not adsorb protein; an antithrombotic coating agent which has superior antithrombotic properties and adhesive properties to a substrate to those of the conventional antithrombotic coating agent; and a medical instrument which is obtained by coating the antithrombotic coating agent, and the block copolymer includes a polymer (A) containing a (meth)acrylic ester monomer and a polymer (B) containing a (meth)acrylamide monomer and has excellent coating formation ability and high adhesive properties to a substrate.

15 Claims, No Drawings

(56) References Cited

OTHER PUBLICATIONS

Search Report mailed Feb. 9, 2015, issued for the European patent application No. 12823466.3.
Katja Skrabania et al., "Synthesis of Double-Hydrophilic BAB Triblock Copolymers via RAFT Polymerisation and their Thermoresponsive Self-Assembly in Water," Macromolecular Chemistry and Physics, 209, 2008, pp. 1389-1403.
John T. Lai et al., "Functional Polymers from Novel Carboxyl-Terminated Trithiocarbonates as Highly Efficient RAFT Agents," Macromolecules, 35, 2002, pp. 6754-6756.
Roshan T. A. Mayadunne et al., "Living Free Radical Polymerization with Reversible Addition-Fragmentation Chain Transfer (RAFT Polymerization): Approaches to Star Polymers" Macromolecules, 36, 2003, pp. 1505-1513.
Graeme Moad et al., "Advances in RAFT polymerization: the synthesis of polymers with defined end-groups," Polymer, 46, 2005, pp. 8458-8468.
International Search Report dated Feb. 12, 2013, issued for PCT/JP2012/070487.
Notice of Allowance dated Feb. 4, 2014, issued for the Japanese patent application No. 2012-173913 and English translation thereof.

* cited by examiner

BLOCK COPOLYMER AND ANTITHROMBOTIC COATING AGENT

TECHNICAL FIELD

The present invention relates to a block copolymer comprising a polymer containing a (meth)acrylic ester monomer and a polymer containing a (meth)acrylamide monomer.

In addition, the present invention relates to an antithrombotic coating agent which is made using the block copolymer and has excellent antithrombotic properties, and a medical instrument coated with the antithrombotic coating agent.

BACKGROUND ART

A block copolymer comprising different kinds of polymer segments expresses properties of the different polymer segments themselves. Therefore, the block copolymer is useful as an adhesive agent, a polymer surfactant, thermoplastic resin, or the like. For example, it is reported that an adhesive composition which contains an A-B type block copolymer comprising a polymer A containing an alkyl(meth)acrylate monomer having an alkyl group having 4 to 12 carbon atoms and a polymer B containing at least one selected from the group consisting of vinyl acetate, methyl acrylate, methyl methacrylate, styrene, and acrylonitrile has high adhesive properties and removability to a flat substrate, and therefore, the adhesive composition does not remain on the substrate after removing (Patent Document No. 1).

In addition, it is also reported that a composition which contains a thermosetting resin and powder or granular A-B type block copolymer comprising a segment A containing a vinyl polymer having a glass transition point of −60 to −20° C. and a segment B containing a vinyl polymer having a glass transition point of 50 to 130° C. has excellent fluidity, and a mold made of the composition has excellent impact resistance and appearance (Patent Document No. 2).

In addition, it is also reported that when an A-B-A type block copolymer containing poly-N-isopropyl acrylamide-poly-N,N-dimethyl acrylamide-poly-N-isopropyl acrylamide is heated to the phase transition temperature (about 32° C.) or more in water, the segment A transfers from hydrophilic to hydrophobic, and thereby the block copolymer is self-coagulated (Non-Patent Document No. 1).

It is considered that the A-B-A type block copolymer is hydrophilic when it is at a temperature less than the phase transition temperature, and does not have adhesive properties to the substrate. However, when it is at the phase transition temperature or more, the segment A transfers to hydrophobic, and thereby has high protein adsorption properties.

In addition, an amide block copolymer which comprises a block made of a repeating unit derived from N,N-dimethyl acrylamide and N-methyl acrylamide and a block made of a repeating unit derived from (meth)acrylic ester monomer having a hydroxyl group or a styrene monomer having a hydroxyl group is useful as a coating agent for a leucocyte-removing filter which can transmit platelets with high transmittance (Patent Document No. 3).

Furthermore, it is also reported that a star block copolymer made of methoxyethyl(meth)acrylate and N-isopropyl acrylamide is water-soluble when it is at the phase transition temperature or less, and becomes hydrophobic when it is at the phase transition temperature or more, an aqueous solution of the star block copolymer at low temperature is coated to a medical instrument, and then the temperature is raised to the phase transition temperature to attach the star block copolymer to the medical instrument; and this technique is used in an antithrombotic instrument (Patent Document No. 4).

As a medical instrument, a polymer (for example, polyolefin resin, such as polypropylene and polyethylene, polyvinyl chloride, polyurethane, polystyrene, polyester, polysulfone, polytetrafluoroethylene), ceramic, metal, and the like, which have high mechanical properties (strength, modulus of elasticity, and ductility) have been used as a main part or a connection part according to the purpose. In particular, it is essential that a medical instrument which is used to directly contact with blood (for example, a catheter, such as a balloon of a balloon catheter, and a guide wire, an artificial blood vessel, a blood vessel bypass tube, an artificial valve, a blood transfusion filter, a plasma separation device, an artificial internal organ, such as an artificial lung, an artificial liver, and an artificial heart, a blood transfusion tool, an extracorporeal circulation blood circuit, a blood bag, a synechia preventive film, a vulnerary covering material, and the like) have blood compatibility with high reliability, in particular, antithrombotic properties for preventing blood coagulation.

However, many materials among those explained above do not have blood compatibility. Therefore, it is essential to use an anticoagulant (for example, heparin) at the same time. However, when influences on a human body or blood are concerned, the continuous availability time of the anticoagulant is limited. Therefore, there is a problem in that there is a time limit for medical activity using such a medical instrument. In order to solve the problem, medical instruments having excellent blood compatibility have been developed. Representative examples of such medical instruments include a medical instrument having a surface in touch with blood on which the anticoagulant such as heparin is immobilized.

However, it is known that when heparin is used, antithrombotic properties are decreased by elution of heparin, and infectious disease can be caused since heparin is generally animal-derived. Therefore, it is most desirable that a material having antithrombotic properties which is free from heparin be developed. However, it is required to utilize properties of various raw materials in the medical instrument. Therefore, it has been desired to develop an antithrombotic coating agent which can provide antithrombotic properties to a product or a part which is made of the raw material explained above.

There are two important factors regarding the coating agent which provides antithrombotic properties. One of them is that the surface coated with the coating agent shows excellent antithrombotic properties, and the other is adhesive properties to the raw material. Regarding the former, when platelets or proteins in blood are attached to the medical instrument, and are activated thereon, clots, so-called thrombus, are formed. There is a risk of severe brain infarction or pulmonary thromboembolism occurring by the thrombus flowing in the blood and being dispersed in the brain or lungs. How to prevent the thrombus formation reaction stably for a long time is a big problem for the antithrombotic coating agent.

In general, it has been considered that a surface having high energy and high wettability (low water contact angle) is suitable as a surface having antithrombotic properties which does not adsorb platelets and the like. For example, it is reported that a surface which is made of a hydrophilic polymer (for example, water-soluble copolymer of polyethylene glycol acrylate and acrylacrylate (Patent Document No. 5)), a copolymer of a hydrophobic monomer and a hydrophilic monomer (for example, a (meth)acrylate copolymer of hydrophobic silicone (meth)acrylate or alkyl(meth) acrylate and hydrophilic(meth)acrylate (Patent Document No. 6)), or hydrophilic hydrogel (for example, chemical crosslinking gel of poly(N,N-dimethyl acrylamide (Patent Document No. 7)) has inhibitory effects which prevent the adhesion of blood components. In addition, it is also reported that an amide block copolymer containing a block having a repeating unit derived from N,N-dimethyl acrylamide or N-methyl acrylamide, and a block having a repeating unit derived from a (meth)acrylic ester monomer having a hydroxyl group or a styrene monomer having a hydroxyl group is useful as a leucocyte-removing filter which transmits the platelets with high transmittance (Patent Document No. 3).

On the other hand, it is also reported that, as the coated material having antithrombotic properties, a member having a surface which includes a synthesized polymer such as methoxyethyl(meth)acrylate having no hydroxyl group prevents the adhesion and activation of the platelets and has antithrombotic properties (Patent Documents No. 8 or 9), and the member is useful as a leucocyte-removing filter (Patent Documents No. 10 or 11), and an artificial lung (Patent Document No. 12). Furthermore, it is also reported that a resin having a repeating unit of methoxyethyl acrylate, such as a block copolymer of methoxyethyl acrylate and N-isopropyl acrylamide (Patent Document No. 4), a block copolymer of methoxyethyl acrylate and glycidyl methacrylate (Patent Document No. 13), and a copolymer of methoxypolyethylene glycol(meth)acrylate and alkyl(meth) acrylate (Patent Document No. 14) can be used as the coating agent having antithrombotic properties. However, even the performance of these materials is insufficient as the coating agent having antithrombotic properties. The market has desired the development of a new excellent antithrombotic material which is free from heparin. In particular, an antithrombotic coating agent which has superior antithrombotic properties to those of a conventional antithrombotic coating agent and high adhesive properties to various substrates has been desired.

PRIOR ART DOCUMENT

Patent Document

Patent Document No. 1: Japanese Unexamined Patent Application, First Publication No. H 10-251609
Patent Document No. 2: Japanese Unexamined Patent Application, First Publication No. 2011-6555
Patent Document No. 3: Japanese Unexamined Patent Application, First Publication No. 2004-339165
Patent Document No. 4: Japanese Unexamined Patent Application, First Publication No. 2008-194363
Patent Document No. 5: Japanese Unexamined Patent Application, First Publication No. H 11-287802
Patent Document No. 6: Japanese Unexamined Patent Application, First Publication No. 2008-289864
Patent Document No. 7: Japanese Unexamined Patent Application, First Publication No. 2008-220786
Patent Document No. 8: Japanese Patent No. 2806510
Patent Document No. 9: Japanese Patent No. 4746984
Patent Document No. 10: Japanese Patent No. 3459836
Patent Document No. 11: Japanese Patent No. 4404445
Patent Document No. 12: Japanese Patent No. 4317183
Patent Document No. 13: Japanese Unexamined Patent Application, First Publication No. 2007-289299
Patent Document No. 14: Japanese Unexamined Patent Application, First Publication No. 2008-264268

Non-Patent Document

Non-Patent Document No. 1: Macromolecular Chemistry and Physics, 209, 1389-1403 (2008)

DISCLOSURE OF THE INVENTION

Problems to be Solved

The first problem to be solved by the present invention is to provide a copolymer, in particular, a block copolymer, which has excellent coating formation ability, adhesive properties to a substrate, and does not adsorb protein.

In addition, the second problem to be solved by the present invention is to provide an antithrombotic coating agent which has superior antithrombotic properties and adhesive properties to a substrate to those of the conventional antithrombotic coating agent, and a medical instrument which is obtained by coating the antithrombotic coating agent.

Means for Solving the Problem

As a result of conducting extensive studies to solve the first problem, the present inventors found that a block copolymer including a polymer (A) containing a (meth) acrylic ester monomer and a polymer (B) containing a (meth)acrylamide monomer has excellent coating formation ability and high adhesive properties to a substrate, and a coating film made of the block copolymer does not adsorb protein. Thereby, the present invention is achieved.

In other words, the present invention provides a block copolymer including a polymer (A) containing a monomer (a) represented by the following general formula (1) and a polymer (B) containing at least one monomer (b) selected from the group consisting of the monomers represented by the following formulae (2) to (7).

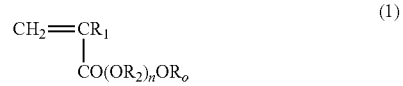

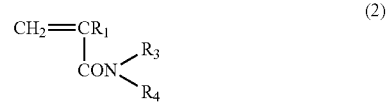

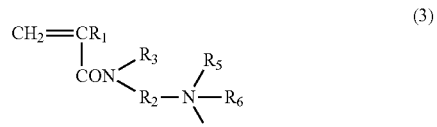

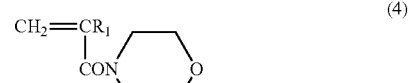

-continued

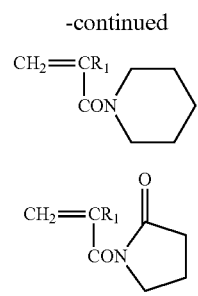

(In the formulae (1) to (7), $R_0$ represents an alkyl group having 1 to 3 carbon atoms; $R_1$ represents a hydrogen atom, or a methyl group; $R_2$ and $R_7$ independently represent an alkylene group having 2 or 3 carbon atoms; $R_3$, $R_4$, $R_5$, and $R_6$ independently represent a hydrogen atom, or an alkyl group having 1 or 2 carbon atoms; X represents a monovalent anion selected from the group consisting of $-CO_2^-$, $-SO_3^-$, $-OSO_3^-$, $-OSO_2^-$, $-OP(=O)(OR_8)O^-$, $-OP(=O))(R_8)O^-$, $-P(=O)(R_8)O^-$, and $-P(=O)(R_8)O^-$; R represents an alkyl group having 1 to 3 carbon atoms; and n represents an integer from 1 to 9.)

In addition, the present invention provides a coating film containing the block copolymer.

In addition, the present invention provides a protein adsorption inhibitor containing the coating film.

Furthermore, the present invention provides a cell culture substrate including the coating film.

In addition, as a result of conducting extensive studies to solve the second problem, the present inventors found that a block copolymer having a specific composition, specifically, a block copolymer including a polymer (A) containing a (meth)acrylate monomer and a polymer (B) or a copolymer (B') containing a (meth)acrylamide monomer, is excellent in both of antithrombotic properties and adhesive properties to a substrate, and achieved the present invention.

Effects of the Present Invention

The block copolymer of the present invention has good balance between hydrophilicity/hydrophobicity of the polymer (A) and the polymer (B) and high solubility or dispersibility in water, in addition to a solvent other than water. Thereby, an aqueous solution or an aqueous dispersion solution having high uniformity can be produced using the block copolymer of the present invention. The aqueous solution or the aqueous dispersion solution of the block copolymer has small physical change, such as change of precipitation, viscosity, and coloring, that is, has high stability. In addition, the block copolymer of the present invention has high film formation properties. The produced film has high transparency and favorable modulus of elasticity, ductility and flexibility. In addition, the coating film made of the block copolymer of the present invention is not only stable in air but also does not swell in water, and has excellent mechanical properties. In addition, since the coating film made of the block copolymer of the present invention has extremely low protein adsorption properties, the coating film is useful as a surface-modifying agent for a cell culture substrate, and medical or biochemical instruments.

In addition, the coating agent of the present invention has high adhesive properties to a substrate. At the same time, the surface of the substrate coated with the coating agent of the present invention has favorable antithrombotic properties. Furthermore, the coating agent of the present invention is stable as a solution or a dispersion solution. The solution or the dispersion solution can be coated uniformly on various substrates. Therefore, the medical instrument coated with the coating agent of the present invention can reliably prevent blood coagulation, and has favorable antithrombotic properties, even when the shape of a part which is in contact with blood is complicated, or the part is in contact with blood for a long period of time.

EMBODIMENTS OF THE PRESENT INVENTION

In order to solve the first problem, the invention according to Claims 1 to 8 has the following compositions.
1. A block copolymer including a polymer (A) containing a monomer (a) represented by the general formula (1) and a polymer (B) containing at least one monomer (b) selected from the group consisting of the monomers represented by the following formulae (2) to (7).

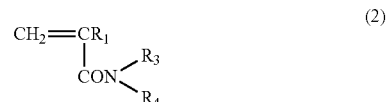

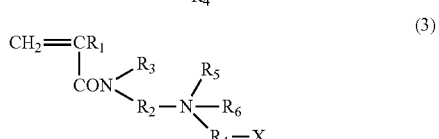

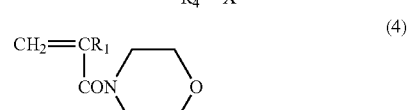

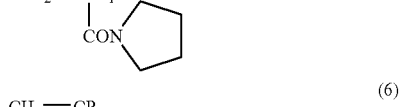

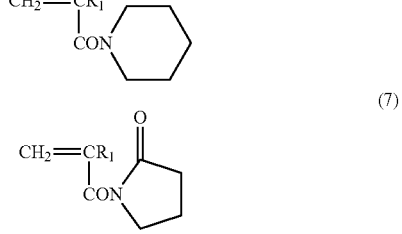

(In the formulae (1) to (7), $R_0$ represents an alkyl group having 1 to 3 carbon atoms; $R_1$ represents a hydrogen atom, or a methyl group: $R_2$ and $R_7$ independently represent an alkylene group having 2 or 3 carbon atoms: $R_3$, $R_4$, $R_5$, and $R_6$ independently represent a hydrogen atom, or an alkyl group having 1 or 2 carbon atoms; X represents a monovalent anion selected from the group consisting of $-CO_2^-$, $-SO_3^-$, $-OSO_3^-$, $-OSO_2^-$, $-OP(=O)(OR_8)O^-$, $-OP(=O)(R_8)O^-$, $-P(=O)(OR_8)O^-$, and $-P(=O)(R_8)O^-$; $R_8$ represents an alkyl group having 1 to 3 carbon atoms; and n represents an integer from 1 to 9.)
2. The block copolymer according to 1, wherein the molar ratio (A:B) between the polymer (A) and the polymer (B) is in a range from 1:50 to 50:1.

3. The block copolymer according to 1 or 2, wherein the polymer (B) is a copolymer including the monomers (b) and (a), and the molar ratio ((b):(a)) between the monomer (b) and the monomer (a) is in a range from 99:1 to 10:90.
4. The block copolymer according to any one of 1 to 3, wherein the block copolymer is any one of a triblock type copolymer, a diblock type copolymer and a multibranched type block copolymer.
5. The block copolymer according to any one of 1 to 4, wherein the polymerization degree of the polymer (A) is in a range from 30 to 3,000, and the polymerization degree of the polymer (B) is in a range from 20 to 20,000.
6. A coating film containing the block copolymer according to any one of 1 to 5.
7. A protein adsorption inhibitor using the coating film according to 6.
8. A cell culture substrate using the coating film according to 6.

As the monomer (a) used in the present invention, (poly)propylene glycol alkyl ether(meth)acrylate, or (poly)ethylene glycol alkyl ether(meth)acrylate is used. The monomer (a) represented by the following general formula (1) is preferably used.

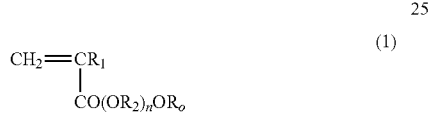
(1)

(In the formula, $R_0$ represents an alkyl group having 1 to 3 carbon atoms; $R_1$ represents a hydrogen atom or a methyl group; $R_2$ represents an alkylene group having 2 or 3 carbon atoms; and n represents an integer from 1 to 9.)

Film-forming properties are afforded to the block copolymer by using the monomer (a). Therefore, a smooth coating film having favorable adhesive properties to a substrate, and wide thickness control range can be obtained by using the monomer (a). The surface of the coating film has low protein adsorption properties.

Among the monomer (a) represented by the general formula (1), one in which n is 1 to 3 is preferable. Specifically, 2-methoxyethyl acrylate, 2-ethoxyethyl acrylate, methyl carbitol acrylate, ethyl carbitol acrylate, methoxytriethylene glycol acrylate, and ethoxytriethylene glycol acrylate are more preferable, and 2-methoxyethyl acrylate, and 2-ethoxyethyl acrylate are most preferable.

The polymer (A) in the present invention is a polymer containing the monomer (a). In the present invention, the polymer (A) preferably contains only monomer (a). However, the polymer (A) can contain another monomer in addition to the monomer (a), as long as the effects of the present invention are not impaired. The polymer (A) preferably contains 65% by mol or more of the monomer (a), and more preferably 95% by mol or more.

Examples of the monomer in addition to the monomer (a) used in the present invention include the monomer represented by the formulae (2) to (7), and a (meth)acrylate monomer having a functional group, such as a hydroxyl group, a glycidyl group, an isocyanate group, a carboxyl group, an amino group, and a sulfonic acid group is preferable.

On the other hand, as the monomer (b) used in the present invention, (meth)acrylamide and/or derivatives thereof, such as N- or N,N substituted (meth)acrylamide. In particular, the acrylamide monomer represented by the following formulae (2) to (7) is preferably used.

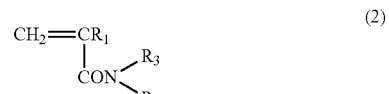
(2)

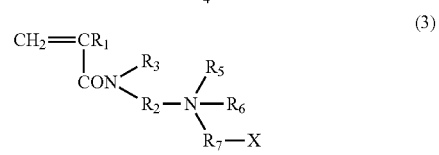
(3)

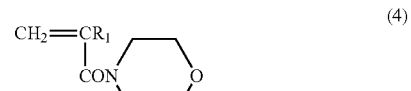
(4)

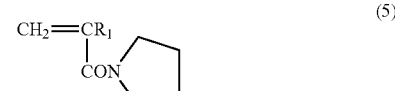
(5)

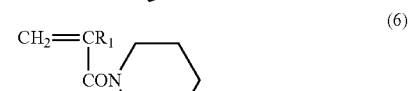
(6)

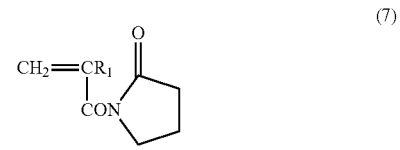
(7)

(In the formulae (1) to (7), $R_0$ represents an alkyl group having 1 to 3 carbon atoms; $R_1$ represents a hydrogen atom, or a methyl group; $R_2$ and $R_7$ independently represent an alkylene group having 2 or 3 carbon atoms; $R_3$, $R_4$, $R_5$, and $R_6$ independently represent a hydrogen atom, or an alkyl group having 1 or 2 carbon atoms; X represents a monovalent anion selected from the group consisting of $-CO_2^-$, $-SO_3^-$, $-OSO_3^-$, $-OSO_2^-$, $-OP(=O)(OR_8)O^-$, $-OP(=O)(R_8)O^-$, $-P(=O)(OR_8)O^-$, and $-P(=O)(R_8)O^-$; $R_8$ represents an alkyl group having 1 to 3 carbon atoms; and n represents an integer from 1 to 9.)

The solubility or the dispersibility to water and stability of the block copolymer which is produced by using the monomer (b) are high, and the film-forming properties of the block copolymer are also favorable. Thereby, a smooth coating film can be obtained. In addition, when N,N-dimethyl acrylamide is used as the monomer (b), a cell has extremely low adhesive properties to the coating film produced. Therefore, the coating film is preferably used for a cell culture under a floating situation.

The polymer (B) contains the monomer (b). The polymer (B) is a polymer which contains only at least one monomer (b) selected from the monomers represented by the formulae (2) to (7), or a copolymer which contains at least one monomer (b) selected from the monomers represented by the formulae (2) to (7) and another monomer. As the other monomer used to produce the copolymer, the monomer (a) is preferably used. The molar ratio (monomer (b):monomer (a)) between the monomers (b) and (a) is preferably in a range of 99:1 to 10:90, more preferably 95:5 to 30:70, most preferably 90:10 to 50:50, and in particular 90:10 to 60:40 is preferable. The copolymer containing the monomers (b) and (a) has an effect such that the block copolymer of the present invention is easily synthesized.

In addition, in order to adjust the balance between hydrophilicity/hydrophobicity or impart a functional group for further inhibiting the interaction to protein of the block copolymer, if necessary, another monomer can be used together with the monomer represented by the general formula (1) and formulae (2) to (7) in the polymer (B) or the copolymer (B). Examples of the monomer used together with the monomer represented by the general formula (1) and formulae (2) to (7) include an acrylic monomer having an anionic group such as a sulfone group and a carboxyl group, an acrylic monomer having a cationic group such as a quaternary ammonium group, an acrylic monomer having an amphoteric ion group, such as a quaternary ammonium group and a phosphate group, an acrylic monomer having an amino acid residue including a carboxyl group and an amino group, an acrylic monomer having a sugar moiety, an acrylic monomer having a hydroxyl group, an acrylic monomer having a polyethylene glycol chain and a polypropylene glycol chain, an amphipathic acrylic monomer having both a hydrophilic chain such as polyethylene glycol and a hydrophobic chain such as nonylphenyl group, polyethylene glycol diacrylate, and N,N'-methylene bisacrylamide.

In the present invention, the arrangement of the polymers (A) and (B) is not limited as long as the block copolymer has properties explained above. For example, A-B type, A-B-A type, B-A-B type, and [B-A]p (p represents the number of branched portions of B, and is preferably in a range of 3 to 10) are preferably used. Among these types, A-B type, A-B-A type, and [B-A]p multibranched type are preferable, and A-B-A type, and [B-A]p multibranched type are more preferable. Moreover, multibranched [B-A]p type means the following structures.

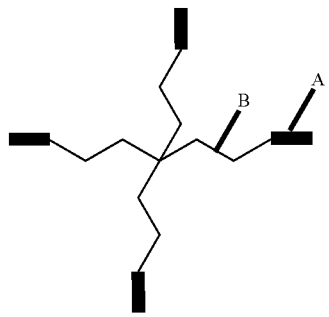

[B-A]$_4$ Type

The molar ratio (A:B) between the polymer (A) and the polymer (B) of the block copolymer of the present invention is preferably in a range of 1:60 to 60:1, more preferably in a range of 1:20 to 20:1, and most preferably in a range of 1:20 to 1:1. When the molar ratio between the polymers (A) and (B) is in the range, the solubility or the dispersibility to water and stability of the block copolymer produced are high, and the film-forming properties of the block copolymer are also favorable. Thereby, a smooth coating film can be obtained. In addition, the protein adsorption properties of the surface of the coating film are low, and cell culturability and removability are favorable, which are preferable.

In addition, in the A-B-A type block copolymer, the polymerization degree of the polymers (A) and (B) is preferably in a range of 30 to 3,000, and 20 to 20,000, respectively, more preferably in a range of 100 to 1,000, and 100 to 5,000, respectively, and most preferably in a range of 100 to 500, and 200 to 2,000, respectively. When the polymerization degree of the polymers (A) and (B) is in the range, the solubility or the dispersibility to water of the block copolymer produced is high, and an aqueous coating agent is easily produced. In addition, film-forming properties are also favorable. Furthermore, the protein adsorption properties of the surface of the coating film produced are low, and cell culturability and removability are favorable, which are preferable.

The method for producing the block copolymer including the polymers (A) and (B) is not particularly limited as long as the monomers (a) and (b) can be polymerized and the block copolymer including the polymers (A) and (B) can be synthesized. Examples of the conventional and common polymerization method include a first method in which the monomer (a) is first polymerized by living radical polymerization using an azo compound and/or organic peroxide as a radical polymerization initiator in the presence of a chain transfer agent (hereinafter referred to as a RAFT agent), such as trithiocarbonate, and then the monomer (b) is polymerized by living radical polymerization to the produced polymer (A), and a second method in which the monomer (b) is polymerized by radical polymerization in the presence of an organic halogen compound and a transition metal complex, the monomer (a) is added, and then these are polymerized by radical polymerization.

In particular, among conventional and common synthesis methods for the block copolymer, the following methods (1-1) to (2-2) are preferable.

(1-1) A method for producing the block copolymer in the first method, wherein after polymerization of the RAFT agent and the monomer (a) in the presence of a small amount of the polymerization initiator, the macro RAFT agent containing only the polymer (A) is obtained by isolation purification, and then the block copolymer is obtained by polymerization of the macro RAFT agent and the monomer (b) in the presence of a small amount of the polymerization initiator.

(1-2) A method for producing the block copolymer in the second method, wherein after polymerization of the monomer (a) in the presence of an organic halogen compound and a transition metal complex, the polymer having a halogen compound at ends containing only the polymer (B) is obtained by the isolation purification, and then the monomer (a) is further polymerized to the polymer produced in the presence of a transition metal complex.

(2-1) A method for producing the block copolymer in the first method, wherein the RAFT agent and the monomer (a) are polymerized in the presence of a small amount of the polymerization initiator, then the monomer (b) is added without the isolation.

(2-2) A method for producing the block copolymer in the second method, wherein the monomer (b) is polymerized in the presence of an organic halogen compound and a transition metal complex, and then the monomer (a) is added without the isolation. In the methods (2-1) and (2-2), it is not necessary to add the latter monomer after the former monomer is completely reacted. The latter monomer may be added at the time that the conversion ratio of the former monomer is about 65% or more. In this case, the polymer produced is a so-called tapered block copolymer in which a part of the monomer (a) and the monomer (b) are mixed, not a perfect block copolymer. However, a polymer having the same functions as those of the perfect block copolymer can be obtained by adequately selecting the molar ratio between the monomer (a) and the monomer (b).

In the present invention, in order to obtain the block copolymer in which the polymer (B) contains the monomer (a) and the monomer (b), a method in which a mixture containing the monomers (a) and (b) are polymerized can be used in addition to the methods (2-1) and (2-2).

Among the protein adsorption properties, when the immunoglobulin G which is previously colored by a TMB color former, the absorbance at 450 nm is preferably 0.5 or less, and more preferably 0.2 or less in the present invention.

In the present invention, various materials can be used as a cell culture substrate. Examples of the material which can be used as the cell culture substrate in the present invention include polypropylene (PP) and polytetrafluoroethylene (PTFE) in addition to polystyrene (PS), polycarbonate (PC), polyethylene terephthalate (PET), and polyurethane (PU). In addition, raw material, such as glass and metal, can also be preferably used. The shape of the substrate can be arbitrarily selected, for example, it may be a plate shape, a straw shape, a thread shape, a spherical shape, and the like. That is, the shape of the coating film can be freely selected.

The block copolymer according to the present invention is useful as a coating, in particular, an aqueous coating, and a surface-modifying agent for a cell culture substrate and various medical or biochemical instruments.

Next, the antithrombotic coating agent according to Claims 9 to 18 to solve the second problem will be explained.

As a result of conducting extensive studies to solve the second problem, the present inventors found that a block copolymer having a specific composition, specifically, a block copolymer including a polymer (A) of a (meth) acrylate monomer and a polymer (B) or a copolymer (B') of a (meth)acrylamide monomer has both excellent antithrombotic properties and high adhesive properties to a substrate, and achieved the present invention. In other words, the present invention to solve the second problems has the following compositions.

9. An antithrombotic coating agent including a block copolymer that includes a polymer (A) containing a monomer (a) represented by the general formula (8), and a polymer (B) containing at least one monomer (b) selected from the group consisting of the monomer represented by the general formulae (9) to (14).

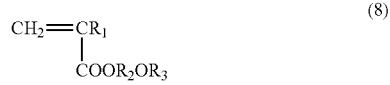

(In the formula (8), $R_1$ represents a hydrogen atom or a methyl group; $R_2$ represents an alkylene group having 2 or 3 carbon atoms; and $R_3$ represents an alkyl group having 1 to 3 carbon atoms.)

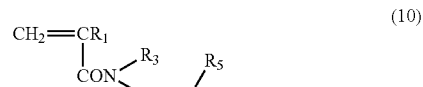

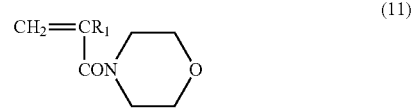

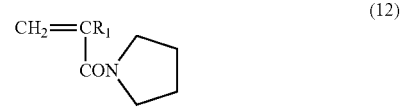

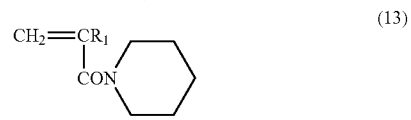

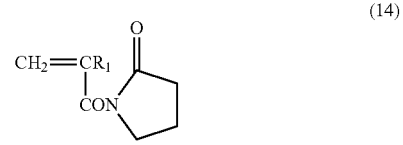

(In the formulae (9) to (14), $R_1$ represents a hydrogen atom, or a methyl group; $R_2$ represents an alkylene group having 2 or 3 carbon atoms $R_3$, $R_4$, $R_5$, and $R_6$ independently represent a hydrogen atom, or an alkyl group having 1 or 2 carbon atoms.)

10. The antithrombotic coating agent according to 9, wherein the block copolymer includes the polymer (A) containing the monomer (a) represented by the general formula (8), and a copolymer (B*) containing the monomer (a) and at least one monomer selected from the group consisting of the monomer (b) represented by the general formulae (9) to (14).

11. The antithrombotic coating agent according to 9 or 10, wherein the polymer (A) is not dissolved in water, and the polymer (B) or the copolymer (B*) is dissolved in water.

12. The antithrombotic coating agent according to 10, wherein the molar ratio (monomer (b)/monomer (a)) between the monomer (b) and the monomer (a) is in a range of 99/1 to 10/90.

13. The antithrombotic coating agent according to 9 or 10, wherein the molar ratio (polymer (A)/polymer (B) or polymer (A)/copolymer (B*)) between the polymer (A) and the polymer (B) or the copolymer (B*) is in a range of 1:50 to 50:1.

14. The antithrombotic coating agent according to any one of 9 to 13, wherein the block copolymer is any one of a triblock type copolymer, a diblock type copolymer, and a multibranched type block copolymer.

15. The antithrombotic coating agent according to 14, wherein the triblock type copolymer is A-B-A type or A-B*-A type; and the multibranched type block copolymer is [B-A]p or [B*-A]p (p represents a number of a branched portion of B or B*, and it is an integer in a range of 3 to 10).

16. The antithrombotic coating agent according to any one of 9 to 15, wherein the polymerization degree of the polymer (A) is in a range of 30 to 3,000, and the polymerization degree of the polymer (B) or the copolymer (B*) is in a range of 20 to 20,000.

17. The antithrombotic coating agent according to any one of 9 to 15, wherein the antithrombotic coating agent includes 0.05 to 10 parts by mass of the block copolymer, and 90 to 99.95 parts by mass of a solvent containing any one of ethanol, methanol, and isopropyl alcohol as a main component.

18. A medical instrument which is coated with the antithrombotic coating agent according to any one of 9 to 17.

As the monomer (a) used in the present invention, propylene glycol alkyl ether(meth)acrylate or ethylene glycol alkyl ether(meth)acrylate, which is represented by the following general formula (8), can be used.

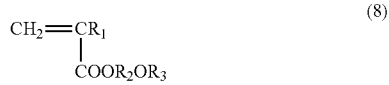

(In the formula (8), $R_1$ represents a hydrogen atom or a methyl group; $R_2$ represents an alkylene group having 2 or 3 carbon atoms; and $R_3$ represents an alkyl group having 1 or 2 carbon atoms.)

Among the monomer (a) represented by the general formula (8), from the viewpoint of the antithrombotic properties and the adhesive properties to the substrate, 2-methoxyethyl acrylate, 2-ethoxyethyl acrylate, 2-methoxyethyl methacrylate, or 2-ethoxyethyl methacrylate is preferable, and 2-methoxyethyl acrylate or 2-ethoxyethyl acrylate is more preferable.

The polymer (A) used in the present invention is a polymer containing the monomer (a). In the present invention, the polymer (A) is preferably a polymer which is polymerized by only the monomer (a). However, in the present invention, it is possible to use another monomer in addition to the monomer (a), as long as the effects of the present invention are not decreased. The polymer (A) is preferably a polymer containing 70% by mol or more of the monomer (a), and more preferably 95% by mol or more.

As the monomer (b) used in the present invention, an acrylamide monomer which is represented by the following formulae (9) to (14), such as (meth)acrylamide or derivatives thereof (N- or N,N substituted (meth)acrylamide), is used.

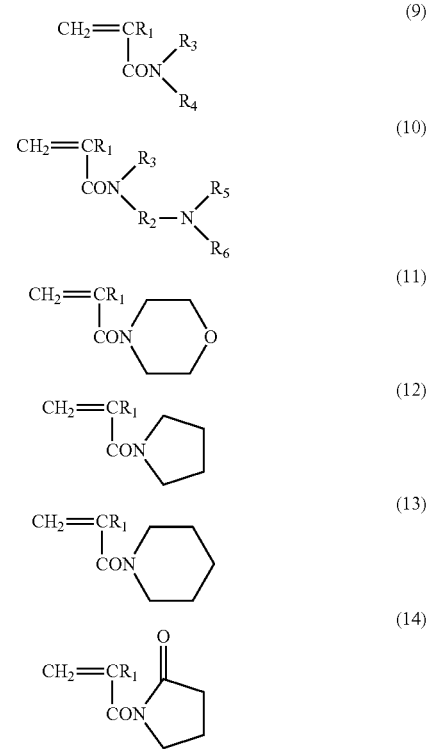

(In the formulae (9) to (14), $R_1$ represents a hydrogen atom, or a methyl group; $R_2$ represents an alkylene group having 2 or 3 carbon atoms; $R_3$, $R_4$, $R_5$, and $R_6$ independently represent a hydrogen atom, or an alkyl group having 1 or 2 carbon atoms.)

The polymer (B) is a polymer containing the monomer (b). As the polymer (B), a polymer containing the monomer (b) represented by the general formulae (9) to (14), or a copolymer (B*) containing the monomer (b) and another monomer. As the other monomer which is used together with the monomer (b), the monomer (a) is preferably used. The molar ratio (monomer (b):monomer (a)) between the monomer (b) and the monomer (a) is 99:1 to 10:90, more preferably 95:5 to 30:70, most preferably 90:10 to 50:50, and in particular 90:10 to 60:40 is preferable. The copolymer (B*) containing the monomer (b) and the monomer (a) can easily produce the block copolymer of the present invention.

In addition, in order to adjust the balance between hydrophilicity and hydrophobicity or impart a functional group for further inhibiting the interaction to protein of the block copolymer, if necessary, another monomer can be used together with the monomer represented by the general formulae (8) to (14) in the polymer (B) or the copolymer (B*).

Examples of the monomer used together with the monomer represented by the general formulae (8) to (14) include an acrylic monomer having an anionic group such as a sulfone group and a carboxyl group, an acrylic monomer having a cationic group such as a quaternary ammonium group, an acrylic monomer having an amphoteric ion group, such as a quaternary ammonium group and a phosphate group, an acrylic monomer having an amino acid residue including a carboxyl group and an amino group, an acrylic monomer having a sugar moiety an acrylic monomer having a hydroxyl group, an acrylic monomer having a polyethylene glycol chain and a polypropylene glycol chain, an amphipathic acrylic monomer having both a hydrophilic chain such as polyethylene glycol and a hydrophobic chain such as nonylphenyl group, polyethylene glycol diacrylate, and N,N'-methylene bisacrylamide.

In the block copolymer of the present invention, it is preferable that the polymer (A) not be dissolved in water, and the polymer (B) or the copolymer (B*) be solved in water.

In the present invention, the block copolymer obtained by using the monomers (a) and (b) has high solubility to an organic solvent having high volatility and low invasiveness to the substrate, such as ethanol, in addition to favorable solubility or dispersibility to water. As a result, the coating agent containing the block copolymer produced has high stability and favorable coating properties (high uniformity and smoothness). In particular, the polymer (a) containing the monomer (a) can further improve the adhesive properties to the substrate when the block copolymer is coated to the substrate, and a smooth coated surface can be obtained. In addition, the coating agent containing the block copolymer can produce a coated surface having excellent antithrombotic properties due to the combined effects of the polymer (A) and the polymer (B) or the polymer (A) and the copolymer (B*).

In the present invention, the arrangement of the polymers (A) and (B) (or the copolymer (B*)) is not limited as long as the block copolymer has properties explained above. For example, a diblock type such as (A-B) and (A-B*), triblock type such as (A-B-A or B-A-B) and (A-B*-A or B*-A-B*), or multibranched type such as ([B-A]p or [B*-A]p (p represents a number of the branched portion of B, and is an integer in a range of 3 to 10) are preferably used. Among these types, A-B type, A-B-A type, [B-A]p type, A-B* type, A-B*-A type, and [B*-A]p type are preferable, A-B-A type, [B-A]p type, A-B*-A type, and [B*-A]p type are more preferable, and A-B-A type and A-B*-A type are most preferable. Moreover, multibranched [B-A]p type means the following structures.

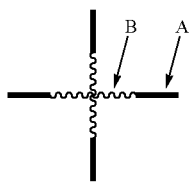

[B-A]p Type

In the present invention, the molar ratio (A:B or B*) between the polymer A and the polymer B or the copolymer (B*) of the block copolymer is preferably in a range of 1:50 to 50:1, more preferably in a range of 1:30 to 30:1, and most preferably in a range of 1:20 to 1:1. When the molar ratio between the polymer (A) and the polymer (B) or the copolymer (B*) is in the range, the solubility of the block copolymer obtained in an organic solvent having high volatility and low invasiveness to the substrate, such as ethanol, is improved. As a result, the coating agent containing the block copolymer produced has favorable coating properties (high uniformity and smoothness) and excellent antithrombotic properties.

In addition, in the block copolymer of the present invention, the polymerization degree of the polymers (A) and (B) (or the copolymer (Be)) is preferably in a range of 30 to 3,000, and 20 to 20,000, respectively, more preferably in a range of 100 to 1,000, and 100 to 5,000, respectively, and most preferably in a range of 100 to 500, and 200 to 2,000, respectively. When the polymerization degree of the polymer (A) and (B) (or the copolymer (B*)) is in the range, the adhesive properties of the block copolymer obtained to the substrate are excellent, and in particular, antithrombotic properties are excellent.

The method for producing the block copolymer of the present invention is not particularly limited as long as the monomers (a) and (b) can be polymerized and the block copolymer including the polymers (A) and (B) (or the copolymer (B*)) can be synthesized. Examples of the conventional and common polymerization method include a first method in which the monomer (a) is first polymerized by living radical polymerization using an azo compound and organic peroxide as a radical polymerization initiator in the presence of a chain transfer agent (hereinafter referred to as RAFT agent), such as trithiocarbonate, and then the monomer (b) is polymerized by living radical polymerization to the produced polymer (A), and a second method in which the monomer (b) is polymerized by radical polymerization in the presence of an organic halogen compound and a transition metal complex, the monomer (a) is added, and then these are polymerized by radical polymerization.

As a solvent used in the antithrombotic coating agent of the present invention, water, an organic solvent, or a mixed solvent containing water and the organic solvent may be used. The kind or the concentration of the solvent used is varied depending on the composition or the molecular weight of the block copolymer obtained, and the kind or surface conditions of the substrate which is coated with the antithrombotic coating agent. However, it is preferable that any one of ethanol, methanol, and isopropanol, which have high volatility and low invasiveness to the substrate, be used as a main component, and the concentration of the solvent be in a range of 90 to 99.95% by mass. In addition, when the antithrombotic coating agent of the present invention is used as an aqueous solution, in order to improve the adhesive properties to the substrate, it is preferable that a surfactant be used at the same time, or the surface of the substrate be subjected to a hydrophilic treatment, such as corona treatment, and a plasma treatment.

In the present invention, various materials can be used as the substrate (for the medical instrument) which is coated with the antithrombotic coating agent. Examples of the material which can be used as the substrate in the present invention include polyolefin resin such as polypropylene and polyethylene, polystyrene, polycarbonate, polyvinyl chloride, polyurethane, polystyrene, polyester, polysulfone, and polytetrafluoroethylene. In addition, glass, ceramic, metal, and the like, can be preferably used. The shape or the conditions of the substrate can be arbitrarily selected, for example, it may be a plate shape, a sheet shape, a straw shape, fibrous, unwoven cloth, or porous. That is, the coating film can be coated uniformly on the substrate.

The coating agent containing the block copolymer of the present invention is used to remarkably improve the antithrombotic properties of a medical instrument which is directly in contact with blood. Specifically, a catheter or the like (catheter, a balloon of a balloon catheter, and a guide wire), an artificial blood vessel, a blood vessel bypass tube, an artificial valve, a blood transfusion filter, a plasma separation device, an artificial internal organ (an artificial lung, an artificial liver, an artificial heart, or the like), a blood transfusion tool, an extracorporeal circulation blood circuit, a blood bag, a synechia preventive film, a vulnerary covering material, and the like, of which the entire or a part of the surface is coated with the antithrombotic coating agent, can be used.

As one representative index for evaluating whether the coating agent is adhered to the surface of the substrate, and effects of the antithrombotic properties due to the adhesion, a blood perfusion test using a tube for blood perfusion which is made of vinyl chloride and a connector for connecting the tube which is made of polycarbonate can be exemplified. It is known that in the case of contacting blood with these parts, and when these are coated with the antithrombotic coating agent, the generation of thrombus is prevented. Therefore, the adhesive properties of the coating on the surface of the substrate can also be evaluated.

Beside the method above, a method for measuring the amount of platelets adsorbed on the surface of the substrate coated with the coating can be used. In this method, whole blood or plate-rich plasma (PRP) which is subjected to an anticoagulant treatment with heparin derived from humans or animals is often used. However, contacting conditions between blood and the surface of the substrate in this method are different from practical clinical conditions. In addition, there is a considerable individual difference of blood when it is measured. Therefore, there is a possibility that this method cannot accurately evaluate the antithrombotic properties.

Accordingly, "a method for measuring elasticity of coagulated blood" and "a method for measuring activity of platelets" are useful as a new method for evaluating antithrombotic properties instead of the method above. The method for measuring elasticity of coagulated blood is carried out by filling a vessel for measurement with whole blood, activating separately the intrinsic factor and the extrinsic factor in coagulated blood, and measuring the variation of elasticity of the thrombus adhered to the substrate when the thrombus is formed by coagulation. In addition, the method for measuring activity of platelets is carried out by filling a vessel for measurement with whole blood, activating platelets in the presence of various factors, and measuring the variation of impedance of the platelets adhered to an electrode. In both methods, the variation caused by blood coagulation is evaluated by using fresh blood. Therefore, it is possible to evaluate under similar conditions to those in real use. The measurement vessel and the like used in the method for measuring elasticity of coagulated blood and the method for measuring activity of platelets are so-called foreign bodies to blood which may cause blood coagulation, just like in vivo. Therefore, when the vessel for measurement and the like are coated with the antithrombotic coating agent, antithrombotic properties can be obtained, that is, blood coagulation or activation of the platelets is inhibited. Compared with a case in which the vessel for measurement and the like which is not coated with the antithrombotic coating agent, the measurement value is expected to be lower.

The Maximum Clot Firmness (MCF) in "the measurement of elasticity of coagulated blood" of the surface coated with the antithrombotic coating agent of the present invention is preferably 40 mm or less, more preferably 20 mm or less, and most preferably 10 mm or less. The area in "the measurement of activity of platelets" is preferably 150 U or less, and more preferably 100 U or less.

EXAMPLES

Below, the present invention is explained in detail referring to Examples. However, the present invention is not limited to the following Examples.

Example 1

Synthesis of Block Copolymer

After bubbling 1.46 g of 2-methoxyethyl acrylate (Toagosei Co. Ltd.) as the monomer (a), 0.0163 g of 2-(dodecyl thiocarbonothioyl thio)-2-methylpropionic acid (Sigma-Aldrich Co. LLC.) as the RAFT agent, 0.0007 g of 2,2'-azobisisobutyronitrile, and 10 mL of 1,4-dioxane with nitrogen, the mixture was stirred at 70° C., for 13 hours. Then, 6.66 g of N,N-dimethyl acrylamide (KOHJIN Holdings Co., Ltd.) as the monomer (b), and 10 mL of 1,4-dioxane were added, and further stirred at 70° C., for 24 hours. After the completion of reaction, the reaction solution was added to diethyl ether. After washing with diethyl ether three times, the reaction product was dried under vacuum, and thereby an A-B type block copolymer was produced.

[Identification of Polymer]

The reaction solution was put in deuterated chloroform, and the $^1$H-NMR spectrum was measured using JNM-LA 300 (JEOL Ltd.). As a result of the measurement, the conversion ratio of the monomers (a) and (b) was 100% and 96%, respectively. In addition, the structure of the produced block copolymer was identified as the structure represented by the formula (15).

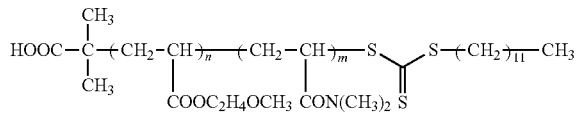

(15)

The theoretical molecular weight of the polymer (A), the polymer (B), and the block copolymer was calculated using the conversion ratios above and the formula (16) below. As a result, the theoretical molecular weight, Mn, of the polymer (A) and the polymer (B) in the A-B type block copolymer, and the A-B type block copolymer was about 32,500 (250 mol), about 143,000 (1440 mol), and about 175,500, respectively.

Theoretical molecular weight, (16)

$$Mn = \text{Conversion ratio} \times \frac{\text{Charge-in quantity of monomer (mmol)}}{\text{Charge-in quantity of RAFT (mmol)}} \times \text{Molecular weight of monomer}$$

[Preparation of Coating Film Containing Block Copolymer]

0.5 g of the produced block copolymer was put in 9.5 g of water, and thereby a polymer solution 1 was obtained. Then, the polymer solution 1 was thinly coated on a petri dish made of polystyrene having a diameter of 35 mm (CORNING, suspension culture dish 430588) and dried. After cleaning the petri dish with sterilized water, a coated petri dish 1 was obtained. When the coated petri dish was visually observed, it was confirmed that the coated petri dish had similar transparency to that of the petri dish before coating.

[Protein Adsorption Properties Test]

1 mL of an aqueous solution of an immunoglobulin G (IgG) marked with HRP was put in the coated petri dish 1, and left at room temperature to adsorb the IgG. After rinsing with a PBS buffer three times, a TMB color former (KPL Co. Ltd.) was added, and then 1N of hydrochloric acid was further added (when protein remains on the surface of the petri dish, color appears). The absorbance at 450 nm of the solution was measured by ultra-violet and visible spectrophotometry (Hitachi, Ltd.), and thereby the adsorption degree of protein was evaluated. The absorbance was 0.157.

[Cell Adhesion Test]

A suitable amount of Ham's F12/10% FCS as a medium was put in the coated petri dish 1, and CHO-K1 cells (fibroblasts derived from an ovary of a Chinese hamster: dissemination concentration: $1\times10^4/cm^2$) were disseminated and cultivated in 5%-carbon dioxide, 37° C., for three days. Then, the medium and floating cells in the petri dish were removed and the petri dish was rinsed with the PBS buffer three times. After that, when the presence of cells adhered to the surface of the petri dish was confirmed using a microscope, the cells were completely washed with the PBS butter, and cells adhered to the surface of the petri dish were not observed.

On the other hand, when the culture examination was carried out using a petri dish made of polystyrene which was not coated in the same manner as above, it was confirmed that a considerable number of cells were adhered to the petri dish.

From the results of the tests above, it was confirmed that the block copolymer had excellent solubility to water, and an aqueous coating could be easily produced. In addition, it was also confirmed that the coating film produced had high transparency and favorable adhesive properties to the substrate, and protein adsorption properties to the surface of the substrate coated were largely inhibited. In addition, it was also found that the adhesive properties of the cells to the surface of the coated film were low, and cells could be cultivated while floating.

Example 2

Synthesis of RAFT Agent

In accordance with Non-Patent Document "Macromolecules, 35, 6754 (2002)" a RAFT agent, 2-(1-carboxy-1-methyl ethyl sulfanyl thiocarbonyl sulfanyl)-2-methyl propionic acid, was synthesized as shown below.

10.1 g of 50%-sodium hydroxide was added to a mixture of 2.62 g of acetone. 5.38 g of trichloromethane, 0.12 g of tetrabutylammonium hydrogen sulfate, 1.37 g of carbon disulfide, and 6 mL of hexane, and the obtained mixture was stirred for 5 hours. After that, the reaction solution obtained was left to rest overnight, and the entire reaction solution was solidified. Then, 45 mL of water was added to dissolve the solidified reaction solution, and 6 mL of concentrated hydrochloric acid was added. A precipitate was obtained by bubbling nitrogen in the solution. After filtrating and washing the precipitate with water, the precipitate was dried. Then, 934 mg of a pale yellow crystal was obtained by recrystallizing with 60%-acetone aqueous solution.

A structure of the RAFT agent obtained was identified as the structure represented by the following formula (17) below by measurement of $^{13}$C-NMR (JEOL Ltd.; JNM-LA300).

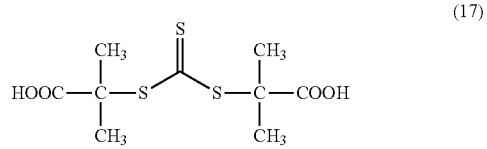

(17)

[Synthesis of Block Copolymer]

After bubbling 2.92 g of 2-methoxyethyl acrylate (Toagosei Co. Ltd.) as a monomer (a), 0.0127 g of 2-(1-carboxy-1-methyl ethyl sulfanyl thiocarbonyl sulfanyl)-2-methyl propionic acid synthesized above as the RAFT agent, 0.0007 g of 2,2'-azobisisobutyronitrile, and 10 mL of 1,4-dioxane with nitrogen, the mixture was stirred at 70° C., for 13 hours. Then, 6.66 g of N,N-dimethyl acrylamide (KOHJIN Holdings Co., Ltd.) as a monomer (b), and 10 mL of 1,4-dioxane were added, and further stirred at 70° C. for 24 hours. The molar ratio (monomer (a):monomer (b)) between the monomer (a) and the monomer (b) was 500:1,500. After the completion of the reaction, the reaction solution was added to diethyl ether. After washing with diethyl ether three times, the reaction product was dried under vacuum, and thereby an A-B-A type block copolymer was produced.

[Identification of Polymer]

Similar to Example 1, the $^{1}$H-NMR spectrum was measured. As a result of the measurement, the conversion ratio of the monomers (a) and (b) was 100% and 99.5%, respectively. In addition, the structure of the produced block copolymer was identified as the structure represented by the formula (18) below.

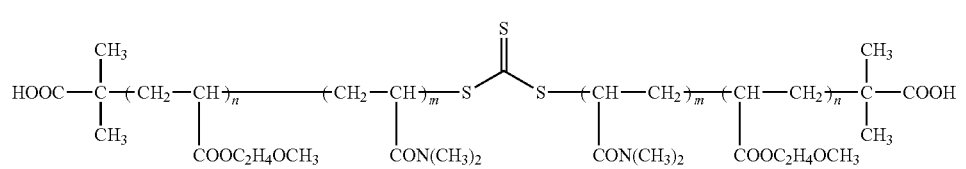

(18)

The theoretical molecular weight of the polymer (A), the polymer (B), and the block copolymer was calculated using the conversion ratios above and the formula (16) above. As a result, the theoretical molecular weight, Mn, of the polymer (A) and the polymer (B) in the A-B-A type block copolymer, and the A-B-A type block copolymer was about 32,500 (250 mol), about 148,000 (1,480 mol), and about 213,000, respectively.

[Preparation of Coating Film Containing Block Copolymer]

Similar to Example 1, a coated petri dish 2 was obtained using the block copolymer obtained. When the coated petri dish 2 was visually observed, it was confirmed that the coated petri dish 2 had similar transparency to that of the petri dish before coating.

[Protein Adsorption Properties Test]

Similar to Example 1, the protein adsorption properties test was carried out using the coated petri dish 2. As a result, the amount of the protein adsorbed (absorbance) was 0.044. In addition, when the protein adsorption properties test was carried out using glass, polycarbonate, and SUS instead of polystyrene as the substrate, the amount of the protein adsorbed was 0.039, 0.073, and 0.076, respectively.

[Cell Adhesion Test]

Similar to Example 1, the cell adhesion test was carried out by cultivating CHO-K1 cells using the coated petri dish 2. As a result, similar to the coated petri dish 1, it was confirmed that the cells were cultivated while floating without adhesion to the surface of the petri dish at all.

According to the results of this Example, it was found that the block copolymer had high solubility in water, and an aqueous coating could be easily produced. In addition, it was also found that the produced coating had high transparency and favorable adhesive properties to the substrate, and adhesion of the protein to the surface coated with the block copolymer was remarkably suppressed. Furthermore, it was found that the adhesion of the cells to the surface coated with the block copolymer was low, and thereby the cells could be cultivated while floating.

Example 3

Synthesis of Block Copolymer

An A-B-A type block copolymer was synthesized in a manner identical to that of Example 2, except that a mixture (molar ratio (a):(b); between the monomer (a) and the monomer (b) was 40:60) of 3.50 g of the monomer (a) and 4.00 g of the monomer (b) was used instead of the monomer (b).

[Identification of Polymer]

Similar to Example 1, the $^1$H-NMR spectrum was measured. As a result of the measurement, the conversion ratio of the monomers (a) and (b) was 100% and 99.1%, respectively.

The theoretical molecular weight of the polymer (A), the polymer (B), and the block copolymer was calculated using the conversion ratios above and the formula (16) above. As a result, the theoretical molecular weight, Mn, of the polymer (A) and the polymer (B) in the A-B type block copolymer, and the A-B type block copolymer was about 32,500 (250 mol), about 166,500 (1490 mol), and about 231,500, respectively.

[Preparation of Coating Film Containing Block Copolymer]

Similar to Example 1, a coated petri dish 3 was obtained using the block copolymer obtained. When the coated petri dish 3 was visually observed, it was confirmed that the coated petri dish 3 had similar transparency to that of the petri dish before coating.

[Protein Adsorption Properties Test]

Similar to Example 1, the protein adsorption properties test was carried out using the coated petri dish 3. As a result, the amount of the protein adsorbed (absorbance) was 0.048.

[Cell Adhesion Test]

Similar to Example 1, the cell adhesion test was carried out by cultivating CHO-K1 cells using the coated petri dish 3. As a result, similar to the coated petri dish 1, it was confirmed that the cells were cultivated while floating without adhesion to the surface of the petri dish at all.

According to the results of this Example, it was found that the block copolymer had high solubility in water, and an aqueous coating could be easily produced. In addition, it was also found that the produced coating had high transparency and favorable adhesive properties to the substrate, and adhesion of the protein to the surface coated with the block copolymer was remarkably suppressed. Furthermore, it was found that the adhesion of the cells to the surface coated with the block copolymer was low, and thereby the cells could be cultivated while floating.

Example 4

Synthesis of Block Copolymer

An A-B-A type block copolymer was synthesized in a manner identical to that of Example 2, except that the polymerization time was changed to 5 hours. After 5 hours had passed from the start of polymerization, the conversion ratio of the monomer (a) measured by $^1$H-NMR was 81%. Thereby, it was found that the polymer (B) contained the monomer (a), which was not reacted during 5 hours of the polymerization, in addition to the monomer (b).

[Identification of Polymer]

Similar to Example 1, the $^1$H-NMR spectrum was measured. As a result of the measurement, the conversion ratio of the monomers (a) and (b) was about 100% and about 99%, respectively.

The theoretical molecular weight of the polymer (A), the polymer (B), and the block copolymer was calculated using the conversion ratios (81%) of the monomer (a), and the formula (16). As a result, the theoretical molecular weight, Mn, of the polymer (A) and the polymer (B) in the A-B-A type block copolymer, and the A-B-A type block copolymer was about 32,500 (200 mol), about 159,400 (1580 mol), and about 224,400, respectively.

[Preparation of Coating Film Containing Block Copolymer]

Similar to Example 1, a coated petri dish 4 was obtained using the block copolymer obtained. When the coated petri dish 4 was visually observed, it was confirmed that the coated petri dish 4 had similar transparency to that of the petri dish before coating.

[Protein Adsorption Properties Test]

Similar to Example 1, the protein adsorption properties test was carried out using the coated petri dish 4. As a result, the amount of the protein adsorbed (absorbance) was 0.046.

[Cell Adhesion Test]

Similar to Example 1, the cell adhesion test was carried out by cultivating CHO-K1 cells using the coated petri dish 4. As a result, similar to the coated petri dish 1, it was confirmed that the cells were cultivated while floating without adhesion to the surface of the petri dish at all.

According to the results of this Example, it was found that the block copolymer had high solubility in water, and an aqueous coating could be easily produced. In addition, it was also found that the produced coating had high transparency and favorable adhesive properties to the substrate, and adhesion of the protein to the surface coated with the block copolymer was remarkably suppressed. Furthermore, it was found that the adhesion of the cells to the surface coated with the block copolymer was low, and thereby the cells could be cultivated while floating.

Example 5

Synthesis of Block Copolymer

An A-B-A type block copolymer was synthesized in a manner identical to that of Example 2, except that the amount of 2-methoxyethyl acrylate as a monomer (a) and N,N-dimethyl acrylamide as a monomer (b) was changed to 5.83 g and 22.21 g, respectively (that is, the molar ratio (a):(b)=1,000:5,000), the polymerization time after adding the monomer (b) was set to 48 hours, and the total amount of 1,4-dioxane was changed to 60 mL (20 mL+40 mL).

[Identification of Polymer]

Similar to Example 1, the $^1$H-NMR spectrum was measured. As a result of the measurement, the conversion ratio of the monomers (a) and (b) was 100% and 97.0%, respectively. In addition, the structure of the produced block copolymer was identified as the structure represented by the formula (11).

The theoretical molecular weight of the polymer (A), the polymer (B), and the block copolymer was calculated using the conversion ratios above and the formula (16). As a result, the theoretical molecular weight, Mn, of the polymer (A) and the polymer (B) in the A-B-A type block copolymer, and the A-B-A type block copolymer was about 65,000 (500 mol), about 480,000 (4,840 mol), and about 610,000.

[Preparation of Coating Film Containing Block Copolymer]

Similar to Example 1, a coated petri dish 5 was obtained using the block copolymer obtained. When the coated petri dish 5 was visually observed, it was confirmed that the coated petri dish had similar transparency to that of the petri dish before coating.

[Protein Adsorption Properties Test]

Similar to Example 1, the protein adsorption properties test was carried out using the coated petri dish 5. As a result, the amount of the protein adsorbed (absorbance) was 0.069.

[Cell Adhesion Test]

Similar to Example 1, the cell adhesion test was carried out by cultivating CHO-K1 cells using the coated petri dish 5. As a result, similar to the coated petri dish 1, it was confirmed that the cells were cultivated while floating without adhesion to the surface of the petri dish at all.

According to the results of this Example, it was found that the block copolymer had high solubility in water, and an aqueous coating could be easily produced. In addition, it was also found that the produced coating had high transparency and favorable adhesive properties to the substrate, and adhesion of the protein to the surface coated with the block copolymer was remarkably suppressed. Furthermore, it was found that the adhesion of the cells to the surface coated with the block copolymer was low, and thereby the cells could be cultivated while floating.

Example 6

Synthesis of Macro-RAFT Agent

After bubbling 5.84 g of 2-methoxyethyl acrylate (Toagosei Co. Ltd.) as a monomer (a), 0.254 g of 2-(1-carboxy-1-methyl ethyl sulfanyl thiocarbonyl sulfanyl)-2-methyl propionic acid which had been synthesized as a RAFT agent, 0.0014 g of 2,2'-azobisisobutyronitrile, and 10 mL of 1,4-dioxane with nitrogen, the mixture was stirred at 70° C. for 18 hours to polymerize. After the completion of the reaction, the reaction solution was added to diethyl ether. After washing a yellow oily product with diethyl ether three times, the reaction product was dried under vacuum, and thereby a macro-RAFT agent containing only the polymer (A) was produced.

[Synthesis of Block Copolymer Using Macro-RAFT Agent]

After bubbling 6.66 g of N,N-dimethyl acrylamide (KOHJIN Holdings Co., Ltd.), 2.69 g of the macro-RAFT agent synthesized at the first stage, 0.0007 g of 2,2'-azobisisobutyronitrile, and 10 mL of 1,4-dioxane with nitrogen, the mixture was stirred at 70° C., for 24 hours. After the completion of the reaction, the reaction solution was added to diethyl ether. After washing the reaction product with diethyl ether three times, the reaction product was dried under vacuum, and thereby an A-B-A type block copolymer was produced.

[Identification of Polymer]

Similar to Example 1, the $^1$H-NMR spectrum was measured. As a result of the measurement, the conversion ratio of the monomers (a) and (b) was about 91.5% and about 94.8%, respectively. In addition, the structure of the produced block copolymer was identified as the structure represented by the formula (18).

The theoretical molecular weight of the polymer (A), the polymer (B), and the block copolymer was calculated using the conversion ratios above and the formula (16). As a result, the theoretical molecular weight, Mn, of the polymer (A) and the polymer (B) in the A-B-A type block copolymer, and the A-B-A type block copolymer was about 30,000 (230 mol), about 141,000 (1,420 mol), and about 201,000, respectively.

[Preparation of Coating Film Containing Block Copolymer]

Similar to Example 1, a coated petri dish 6 was obtained using the block copolymer obtained. When the coated petri dish 6 was visually observed, it was confirmed that the coated petri dish had similar transparency to that of the petri dish before coating.

[Protein Adsorption Properties Test]

Similar to Example 1, the protein adsorption properties test was carried out using the coated petri dish 6. As a result, the amount of the protein adsorbed (absorbance) was 0.058.

[Cell Adhesion Test]

Similar to Example 1, the cell adhesion test was carried out by cultivating CHO-K1 cells using the coated petri dish 6. As a result, similar to the coated petri dish 1, it was confirmed that the cells were cultivated while floating without adhesion to the surface of the petri dish at all.

Example 7

Synthesis of Block Copolymer

An A-B-A type block copolymer was synthesized in a manner identical to that of Example 2, except that 6.00 g of N,N'-dimethyl acrylamide and 1.05 g of N,N-dimethyl aminopropyl acrylamide (KOHJIN Holdings Co. Ltd.) were added as the monomer (b). After that, 1.017 g of the synthesized block copolymer was dissolved in 5 mL, of acetonitrile, and 742 mg of 1,3-propane sultone was added. Then, the mixture was left at room temperature to rest for 7 days. The solution obtained was added to ethyl ether, and a white precipitate was produced. After washing with diethyl ether three times, the reaction product was dried under vacuum, and thereby 746 mg of white powder, a block copolymer having a 3-(N,N-dimethyl-N-(3-sulfopropyl)ammonio)propyl group, was produced.

[Identification of Polymer]

Similar to Example 1, the $^1$H-NMR spectrum of the produced A-B-A type block copolymer was measured. As a result of the measurement, the conversion ratio of the monomers (a), the N,N-dimethyl acrylamide monomer, and the N,N-dimethyl aminopropyl acrylamide monomer was 100%, 95%, and 85%, respectively. In addition, the structure of the produced block copolymer was identified as the structure represented by the formula (19) below.

The theoretical molecular weight of the polymer (A), the copolymer (B), and the block copolymer was calculated using the conversion ratios above and the formula (16) below. As a result, the theoretical molecular weight. Mn, of the polymer (A) and the copolymer (B) in the A-B-A type block copolymer, and the A-B-A type block copolymer was about 32,500 (250 mol), about 162,000 (1,410 mol), and about 227,000, respectively.

(19)

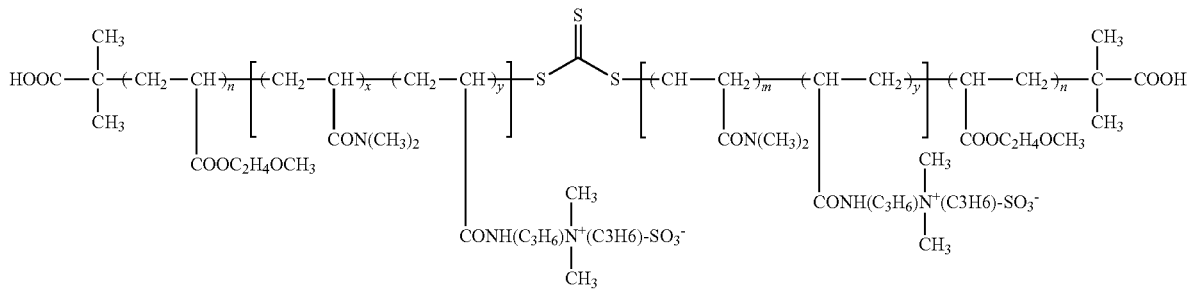

[Preparation of Coating Film Containing Block Copolymer]

Similar to Example 1, a coated petri dish 7 was obtained using the block copolymer obtained. When the coated petri dish 7 was visually observed, it was confirmed that the coated petri dish had similar transparency to that of the petri dish before coating.

[Protein Adsorption Properties Test]

Similar to Example 1, the protein adsorption properties test was carried out using the coated petri dish 7. As a result, the amount of the protein adsorbed (absorbance) was 0.090.

[Cell Adhesion Test]

Similar to Example 1, the cell adhesion test was carried out by cultivating CHO-K1 cells using the coated petri dish 7. As a result, similar to the coated petri dish 1, it was confirmed that the cells were cultivated while floating without adhesion to the surface of the petri dish at all.

According to the results of this Example, it was found that the block copolymer had high solubility in water, and an aqueous coating could be easily produced. In addition, it was also found that the produced coating had high transparency and favorable adhesive properties to the substrate, and adhesion of the protein to the surface coated with the block copolymer was remarkably suppressed. Furthermore, it was found that the adhesion of the cells to the surface coated with the block copolymer was low, and thereby the cells could be cultivated while floating.

Example 8

Synthesis of RAFT Agent

In accordance with Non-Patent Document "Macromolecules, 36, 1505 (2003)" a RAFT agent, tetrakis(3-1S-(1-methoxycarbonyl)ethyl trithiocarbonyl propionate)penthaerythritol, was synthesized.

10 mL of dichloromethane, 1.22 g of pentaerythritol (3-mercaptopropionate), 2.00 g of carbon disulfide, and 2.04 g of triethylamine were added to the obtained mixture, and stirred for 1 hour. After adding 1.94 g of methyl 2-bromopropionate, the solution was further stirred for 5 hours, and the reaction solution was washed with 5%-KHSO$_4$ aqueous solution. After further washing with water, the reaction product was dried using an unsaturated salt solution. After treatment with magnesium sulfate, dichloromethane was removed by an evaporator. An orange oily reaction product was purified by silica gel column-chromatography using hexane/acetone as an eluent. Thereby, a RAFT agent, tetrakis(3-1S-(1-methoxycarbonyl)ethyl trithiocarbonyl propionate)penthaerythritol, was produced. A structure of the RAFT agent obtained was identified as the structure shown by the following formula (20) below by measurement of $^1$H-NMR.

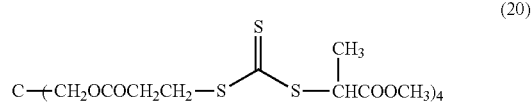

[Synthesis of Multibranched Type Block Copolymer]

A [B-A]$_4$ multibranched type block copolymer was synthesized in a manner identical to that of Example 2, except that the amount of 2-methoxyethyl acrylate as a monomer (a) and N,N-dimethyl acrylamide as a monomer (b) was changed to 2.92 g and 6.66 g, respectively (that is, the molar ratio (a):(b)=250:750), and 0.0255 g of the compound represented by the formula (20) as a RAFT agent was used.

[Identification of Polymer]

Similar to Example 1, the $^1$H-NMR spectrum was measured. As a result of the measurement, the conversion ratio of the monomers (a) and (b) was 100% and 99.0%, respectively. In addition, the structure of the produced block copolymer was identified as the structure represented by the formula (21) below.

The theoretical molecular weight of the polymer (A) and the polymer (B), and the [B-A]$_4$ multibranched type block copolymer was calculated using the conversion ratios above and the formula (16). As a result, the theoretical molecular weight, Mn, of the polymer (A) and the polymer (B) in the [B-A]$_4$ multibranched type block copolymer, and the [B-A]$_4$ multibranched type block copolymer was about 32,500 (250 mol), about 73,300 (740 mol), and about 423,200.

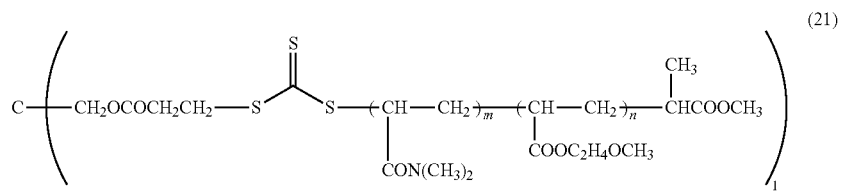

[Preparation of Coating Film Containing Block Copolymer]

0.5 g of the produced block copolymer was added to 9.5 g of water, and thereby a polymer solution 8 was obtained. Then, the polymer solution 8 was poured in a 15-mL precipitation tube for centrifugal separation (AS ONE Corporation) made of polypropylene to coat the inside wall of the tube, and dried. After cleaning the precipitation tube, a coated precipitation tube 8 was obtained. When the coated precipitation tube 8 was visually observed, it was confirmed that the coated precipitation tube had similar transparency to that of the tube before coating.

[Protein Adsorption Properties Test]

Similar to Example 1, the protein adsorption properties test was carried out using the coated precipitation tube 8. As a result, the amount of the protein adsorbed (absorbance) was 0.056.

According to the results of this Example, it was found that the multibranched block copolymer had high solubility in water, and an aqueous coating could be easily produced. In addition, it was also found that the produced coating could be easily coated on a polypropylene substrate and had favorable adhesive properties to the substrate, and adhesion of the protein to the surface coated with the block copolymer was remarkably suppressed.

Example 9

Synthesis of Multibranched Block Copolymer

A [B-A]$_4$ multibranched type block copolymer was synthesized in a manner identical to that of Example 8, except that the polymerization time was changed to 4 hours. After 4 hours had passed from the start of polymerization, the conversion ratio of the monomer (a) measured by $^1$H-NMR was 75%. Thereby, it was found that the polymer (B) contained the monomer (a), which was not reacted during 4 hours of the polymerization, in addition to the monomer (b).
[Identification of Polymer]

Similar to Example 1, the $^1$H-NMR spectrum was measured. As a result of the measurement, the conversion ratio of the monomers (a) and (b) was 100% and 98.5%, respectively. In addition, the structure of the produced block copolymer was identified as the structure represented by the formula (22) below.

The theoretical molecular weight of the polymer (A), the polymer (B), and the block copolymer was calculated using the conversion ratios above and the formula (16). As a result, the theoretical molecular weight, Mn, of the polymer (A) and the polymer (B) in the A-B-A type block copolymer, and the A-B-A type block copolymer was about 32,500 (250 mol), about 210,000 (1,490 mol), and 275,000.

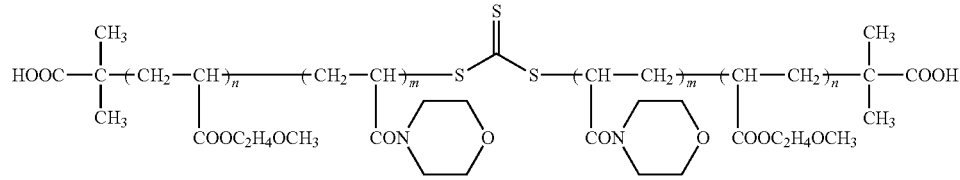

(22)

Similar to Example 1, the $^1$H-NMR spectrum was measured. As a result of the measurement, the conversion ratio of the monomers (a) and (b) was about 100% and about 97.2%, respectively.

The theoretical molecular weight of the polymer (A), the copolymer (B), and the block copolymer was calculated using the conversion ratios (75%) of the monomer (a), and the formula (16). As a result, the theoretical molecular weight, Mn, of the polymer (A) and the copolymer (B) in the [B-A]$_4$ multibranched type block copolymer, and the [B-A]$_4$ multibranched type block copolymer was about 24,400 (190 mol), about 80,100 (790 mol), and about 418,000.
[Preparation of Coating Film Containing Block Copolymer]

Similar to Example 8, a coated precipitation tube for centrifugal separation 9 was obtained using the block copolymer obtained. When the coated precipitation tube for centrifugal separation 9 was visually observed, it was confirmed that the coated precipitation tube had similar transparency to that of the petri dish before coating.
[Protein Adsorption Properties Test]

Similar to Example 1, the protein adsorption properties test was carried out using the coated precipitation tube 9. As a result, the amount of the protein adsorbed (absorbance) was 0.060.

According to the results of this Example, it was found that the multibranched block copolymer had high solubility in water, and an aqueous coating could be easily produced. In addition, it was also found that the produced coating could be easily coated on a polypropylene substrate and had favorable adhesive properties to the substrate, and adhesion of the protein to the surface coated with the block copolymer was remarkably suppressed.

Example 10

Synthesis of Block Copolymer

An A-B-A type block copolymer was synthesized in a manner identical to that of Example 2, except that 9.49 g of acryloyl morpholine was used as the monomer (b) instead of N,N-dimethyl acrylamide.

[Preparation of Coating Film Containing Block Copolymer]

Similar to Example 1, a coated petri dish 10 was obtained using the block copolymer obtained. When the coated petri dish 10 was visually observed, it was confirmed that the coated petri dish had similar transparency to that of the petri dish before coating.
[Protein Adsorption Properties Test]

Similar to Example 1, the protein adsorption properties test was carried out using the coated petri dish 10. As a result, the amount of the protein adsorbed (absorbance) was 0.102.
[Cell Adhesion Test]

Similar to Example 1, the cell adhesion test was carried out by cultivating CHO-K1 cells using the coated petri dish 10. As a result, similar to the coated petri dish 1, it was confirmed that the cells were cultivated while floating without adhesion to the surface of the petri dish at all.

According to the results of this Example, it was found that the block copolymer had high solubility in water, and an aqueous coating could be easily produced. In addition, it was also found that the produced coating had high transparency and favorable adhesive properties to the substrate, and adhesion of the protein to the surface coated with the block copolymer was remarkably suppressed. Furthermore, it was found that the adhesion of the cells to the surface coated with the block copolymer was low, and thereby the cells could be cultivated while floating.

Example 11

Synthesis of Block Copolymer

An A-B-A type block copolymer was synthesized in a manner identical to that of Example 2, except that the molar ratio ((a):(b)) between the monomer (a) and the monomer (b) was changed to 500:15,000 by using 2.92 g of 2-methoxyethyl acrylate as a monomer (a) and 66.62 g of N,N-dimethyl acrylamide as a monomer (b), the polymerization time after adding the monomer (b) was set to 72 hours, and the total amount of 1,4-dioxane was changed to 100 mL (20 mL+80 mL).

[Identification of Polymer]

Similar to Example 1, the $^1$H-NMR spectrum was measured. As a result of the measurement, the conversion ratio of the monomers (a) and (b) was 100% and 93.0%, respectively. In addition, the structure of the produced block copolymer was identified as the structure represented by the formula (18).

The theoretical molecular weight of the polymer (A), the polymer (B), and the block copolymer was calculated using the conversion ratios above and the formula (16). As a result, the theoretical molecular weight, Mn, of the polymer (A) and the polymer (B) in the A-B-A type block copolymer, and the A-B-A type block copolymer was about 32,500 (polymerization degree: 250 mol), about 1,381,000 (polymerization degree: 13,940 mol), and about 1,446,000.

[Preparation of Coating Film Containing Block Copolymer]

Similar to Example 1, a coated petri dish 11 was obtained using the block copolymer obtained. When the coated petri dish 11 was visually observed, it was confirmed that the coated petri dish had similar transparency to that of the petri dish before coating.

[Protein Adsorption Properties Test]

Similar to Example 1, the protein adsorption properties test was carried out using the coated petri dish 11. As a result, the amount of the protein adsorbed (absorbance) was 0.320.

[Cell Adhesion Test]

Similar to Example 1, the cell adhesion test was carried out by cultivating CHO-K1 cells using the coated petri dish 11. As a result, similar to the coated petri dish 1, it was confirmed that the cells were cultivated while floating without adhesion of almost all of the cells on the surface of the petri dish.

According to the results of this Example, it was confirmed that when the molar ratio ((A):(B)) between the polymer (A) and the polymer (B) exceeded 1:20, the adhesion properties of the cells to the surface coated with the block copolymer was maintained at a low level, and the amount of protein adsorbed tended to increase.

Example 12

Synthesis of Raw Material of RAFT Agent

In accordance with Non-Patent Document "Polymer, 46, 8458 (2005)" a RAFT agent, sodium s-dodecyl trithiocarbonate, was synthesized.

While stirring, 1.18 g of 60%-sodium hydroxide was added to 75 mL of diethyl ether. Under ice-cold conditions, when 5.48 g of dodecyl mercaptan was added, and then 2.42 g of carbon disulfide was further added, a yellow raw material of a RAFT agent was immediately produced. Whilst the product was still cold, the reaction product was filtrated, washed with cold diethyl ether, dried under vacuum, and thereby 6.14 g of yellow power was produced.

[Synthesis of RAFT Agent]

226 mg of 14-bisbromomethyl benzene was dissolved in 10 mL of toluene, and 662 mg of the raw material of a RAFT agent was added over several additions. After stirring at room temperature for 4 hours, the reaction solution was left to rest overnight, 5 mL of hexane was added, and then washed with a saturated sodium bicarbonate aqueous solution. After further washing with water, the reaction product was dried using an unsaturated salt solution. After treatment with magnesium sulfate, toluene and hexane were removed by an evaporator. Yellow powder produced was recrystallized using hexane, and thereby a RAFT agent, 1,4-bis (dodecyl sulfanyl thiocarbonyl sulfanyl methyl)benzene which was denoted by the formula (23) below, was produced.

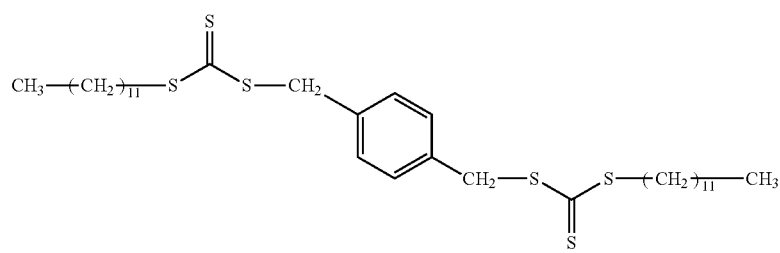

(23)

[Synthesis of Block Copolymer]

After bubbling 0.22 g of N,N-dimethyl acrylamide as a monomer (b), 0.0295 g of 1,4-bis(dodecyl sulfanyl thiocarbonyl sulfanyl methyl)benzene synthesized above as a RAFT agent, 0.0007 g of 2,2-azobisisobutyronitrile, and 10 mL of 1,4-dioxane with nitrogen, the mixture was stirred at 70° C. for 13 hours. Then, 2.92 g of 2-methoxyethyl acrylate as a monomer (a) (that is, the molar ratio (a):(b)=500:50), and 10 mL of 1,4-dioxane were added, and further stirred at 70° C., for 24 hours. After the completion of the reaction, the reaction solution was added to diethyl ether. After washing with diethyl ether three times, the reaction product was dried under vacuum, and thereby an A-B-A type block copolymer was produced.

[Identification of Polymer]

Similar to Example 1, the $^1$H-NMR spectrum was measured. As a result of the measurement, the conversion ratio of the monomers (a) and (b) was 100% and 97.0%, respectively. In addition, the structure of the produced block copolymer was identified as the structure represented by the formula (24) below.

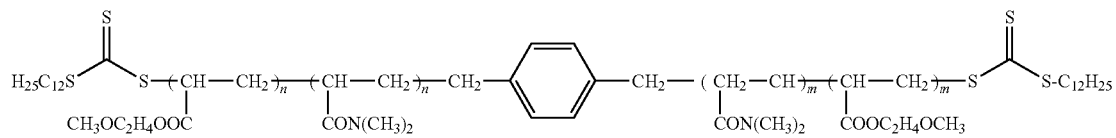

(24)

The theoretical molecular weight of the polymer (A), the polymer (B), and the block copolymer was calculated using the conversion ratios above and the formula (16) below. As a result, the theoretical molecular weight, Mn, of the polymer (A) and the polymer (B) in the A-B-A type block copolymer, and the A-B-A type block copolymer was about 32,500 (polymerization degree: 250 mol), about 4,800 (polymerization degree: 48 mol), and about 70,000.

[Preparation of Coating Film Containing Block Copolymer]

Similar to Example 1, a coated petri dish 12 was obtained using the block copolymer obtained. When the coated petri dish 12 was visually observed, it was confirmed that the coated petri dish had similar transparency to that of the petri dish before coating.

[Protein Adsorption Properties Test]

Similar to Example 1, the protein adsorption properties test was carried out using the coated petri dish 12. As a result, the amount of the protein adsorbed (absorbance) was 0.310.

[Cell Adhesion Test]

Similar to Example 1, the cell adhesion test was carried out by cultivating CHO-K1 cells using the coated petri dish 12. As a result, it was confirmed that a small amount of the cells were adhered to the surface of the petri dish.

According to the results of this Example, it was found that when the molar ratio ((A):(B)) between the polymer (A) and the polymer (B) was less than 1:0.5, the amount of the protein adsorbed to the surface coated with the block copolymer tended to increase, and the adhesive properties of the cells to the surface coated also tended to increase.

Example 13

Coating of Substrate 0.1 g of the block copolymer produced in Example 2 was added to 10 g of ethanol, and stirred, thereby a colorless and transparent polymer solution was produced. Then, a suitable quantity of the polymer solution was poured into a tube made of polyvinyl chloride having a diameter of ⅜ inches and length of 30 cm (MERA exceline: Senko Medical Instrument Mfg. Co., Ltd.), and the state was held for 5 minutes to coat the inside of the tube. After removing the polymer solution from the tube, the tube was dried in a hot gas dryer at 50° C. for 15 minutes. Then, the coated tube was immersed in sterilized water at 50° C. and the temperature was maintained at 50° C. to wash the tube. After washing, the tube was put in a hot gas dryer at 50° C. again, dried for 30 minutes, and thereby a coated tube was produced. When the coated tube was observed visually or using a microscope, it was confirmed that the coating film was uniform and had high transparency.

In addition, a connector for the tube, which was made of polycarbonate and had projections and recesses (connector for MERA artificial cardiopulmonary; Senko Medical Instrument Mfg. Co. Ltd.), was also immersed in the polymer solution to coat similar to the tube above. Thereby, a coated connector was produced.

[Adsorption Properties Test of Protein in Blood]

Using the coated tube which was produced above, the adsorption properties test of the protein in blood was carried out. 5 mL of venous blood was collected from an adult beef bull using a syringe. Just after collecting the venous blood, 100 mL of a heparin sodium injection (HEPARIN SODIUM INJECTION 100000 UNITS®: Mitsubishi Tanabe Pharma Corporation) was added to anticoagulate. On the other hand, the coated tube was cut to 3 cm in length. 1 mL, of the anticoagulated blood was filled in the coated tube, and both ends thereof were sealed. Then, the tube was maintained for 30 minutes in an incubator at 37° C. while shaking. After discharging the blood in the tube, the tube was lightly washed with an isotonic sodium chloride solution. The coated tube after washing was immersed in a 2%-glutaraldehyde aqueous solution, and maintained at room temperature for 1 hour. After that, the coated tube was removed, and cut to 1 cm length. When the amount of the protein on an inner surface of the tube was measured by Micro BCA Protein Assay Kit (Thermo SCIENTIFIC), the result was 7.5 μg/cm². This amount of the protein adsorbed was remarkably small.

[Blood Perfusion Test]

Using the coated tube and the coated connectors which were produced above, a fresh bovine blood perfusion test was carried out. Specifically, 5 mL of venous blood was collected from an adult beef bull using a syringe. Just after collecting the venous blood, the blood was filled in the coated tube, and both ends of the tube were connected using the connector so as to make a loop. The looped tube was immersed in a constant-temperature water bath at 37° C., and the blood was perfused in the tube at 100 rpm. After 15 minutes, the rotation was stopped, and the tube was removed from the constant-temperature water bath. Then, the connectors were removed from both ends of the tube, and the blood filled in the tube was collected. The bovine blood collected was not solidified, and had fluidity. When the surface of the coated tube and the coated connectors after removing blood were lightly washed with an isotonic sodium chloride solution, and the inside surface thereof was observed visually or using a microscope, generation of thrombus was not confirmed. Then, the coated tube was cut to 2 cm in length, and immersed in a 2%-glutaraldehyde aqueous solution, and maintained at room temperature for 1 hour. After that, the coated tube was removed, washed with an isotonic sodium chloride solution to remove glutaraldehyde, and dried at room temperature. Then, when the inside surface of the tube was observed using SEM, the protein components derived from blood, such as blood corpuscles, platelets, and plasma, were not observed. In other words, the tube and the connectors were completely coated with the block copolymer, the coating was adhered to the substrate during blood perfusion, without peeling, and the block copolymer had antithrombotic properties. From these results, it was confirmed that the block copolymer had excellent adhesive properties to the substrate made of polyvinyl chloride or polycarbonate.

[Blood Cell Counting Test]

1 mL of the venous blood was collected from the same adult beef bull in the same manner as that of the blood perfusion test. When the number of the platelets in the venous blood was counted using a blood cell counting device (Laser Cite: IDEXX Laboratories), the result was $535 \times 10^3/\mu L$. In addition, when the number of the platelets in the bovine blood after the blood perfusion test was counted using the blood cell counting device in the same manner above, the result was $550 \times 10^3/\mu L$, which substantially equaled the number before the blood perfusion test.

[Elasticity Measurement of Coagulated Blood]

Using a whole blood coagulation/fibrinolysis analyzer, Thromboelastometry (ROTEM®: FINGGAL LINK Co. Ltd.), the change of elasticity of blood due to coagulation was measured. Specifically, the block copolymer was coated to the outside surface of a cup and a pin for ROTEM measurement in the same manner as that of "Coating of Substrate" above. Human fresh blood, which was provided from volunteers, and a certain amount of a blood coagulation facilitator were added to the coated cup and set in the device. Thereby, the elasticity behavior of blood when the blood was coagulated using the coated cup and the coated pin was measured. As a result, a peak showing coagulation starting began to be visible after about 3 minutes from the start of the measurement. However, the peak was very small (the MCF of the peak was 7 mm). In addition, the peak for showing blood coagulation became smaller 2 minutes after the peak was observed, and the peak completely disappeared after several minutes. After 30 minutes, the measurement was finished. When the inside of the cup was observed, the blood was coagulated. Thereby, it was confirmed that the measurement was correctly carried out. In addition, it was also confirmed that the blood coagulation which was started by the blood coagulation facilitator was not promoted, and the adhesion of the thrombus to the cup and the pin due to the blood coagulation was remarkably inhibited. According to these results, it was confirmed that the cup and the pin were reliably coated with the block copolymer, the coating was adhered to the surface of the substrate during the measurement without peeling, and had antithrombotic properties, and thereby, the block copolymer had favorable adhesive properties to the substrate made of polypropylene.

[Platelet Activity Measurement]

The aggregation ability of the platelets by the impedance method was measured using a platelet aggregation rate test instrument (Multiplate: Verum). The block copolymer was coated to the inside surface of a cup which was made of polypropylene and provided with a metal electrode for Multiplate and a stirrer which was made of polytetrafluoroethylene (PTFE) in the same manner as that of "Coating of Substrate" above. Human fresh blood, which was provided by volunteers, and a certain amount of a platelet activation reagent were added to the coated cup and adhered to the coated stirrer and they were set in the device. Thereby, the change of impedance due to the platelet aggregation was measured. As a result, the change of the impedance was hardly observed from the start of the measurement. Within 15 minutes from the start of the measurement, the area was 20 U. Thereby, it was found that the platelet activity and aggregation were largely inhibited. In addition, according to these results, it was also confirmed that the cup which was made of polypropylene and provided with the metal electrode, and the PTFE stirrer were reliably coated with the block copolymer, and the coating was adhered to the surface of the substrate during the measurement without peeling, and had antithrombotic properties, and thereby, the block copolymer had favorable adhesive properties to the substrate made of polypropylene or PTFE.

Example 14

Coating of Substrate

A coated tube and coated connectors were produced using the block copolymer produced in Example 5 in a manner identical to that of Example 13. When the coated tube and coated connectors were observed visually or using a microscope, the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition, "Elasticity Measurement of Coagulated Blood", and "Platelet Activity Measurement" were also carried out by coating a measurement vessel with the block copolymer in a manner identical to that of Example 13. The results are shown in Table 2.

Example 15

Coating of Substrate

A coated tube and coated connectors were produced using the block copolymer produced in Example 3 in a manner identical to that of Example 13. When the coated tube and coated connectors were observed visually or using a microscope, the coating was uniform and had high transparency.

[Evaluation of Antithrombotic Properties]

Using the coated tube and coated connectors which were produced above, "Protein Adsorption Properties Test", "Blood Perfusion Test", and "Blood Cell Counting Test" were carried out in a manner identical to that of Example 13. In addition, "Elasticity Measurement of Coagulated Blood", and "Platelet Activity Measurement" were also carried out by coating a measurement vessel with the block copolymer in a manner identical to that of Example 13. The results are shown in Table 2.

Example 16

Coating of Substrate

A coated tube and coated connectors were produced using the block copolymer produced in Example 4 in a manner identical to that of Example 13. When the coated tube and coated connectors were observed visually or using a microscope, the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition, "Elasticity Measurement of Coagulated Blood", and "Platelet Activity Measurement" were also carried out by coating a measurement vessel with the block copolymer in a manner identical to that of Example 13. The results are shown in Table 2.

Example 17

Coating of Substrate

A coated tube and coated connectors were produced using the block copolymer produced in Example 8 in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above, "Adsorption Properties Test of Protein in Blood". "Blood Perfusion Test", and "Blood Cell Counting Test" were carried out in a manner identical to that of Example 13. In addition. "Elasticity Measurement of Coagulated Blood", and "Platelet Activity Measurement" were also carried out by coating a measurement vessel with the block copolymer in a manner identical to that of Example 13. The results are shown in Table 2.

Example 18

Coating of Substrate

A coated tube and coated connectors were produced using the block copolymer produced in Example 9 in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition, "Elasticity Measurement of Coagulated Blood", and "Platelet Activity Measurement" were also carried out by coating a measurement vessel with the block copolymer in a manner identical to that of Example 13. The results are shown in Table 2.

Example 19

Coating of Substrate

A coated tube and coated connectors were produced using the block copolymer produced in Example 1 in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition. "Elasticity Measurement of Coagulated Blood", and "Platelet Activity Measurement" were also carried out by coating a measurement vessel with the block copolymer in a manner identical to that of Example 13. The results are shown in Table 2.

Example 20

Coating of Substrate

A coated tube and coated connectors were produced using the block copolymer produced in Example 10 in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition. "Elasticity Measurement of Coagulated Blood", and "Platelet Activity Measurement" were also carried out by coating a measurement vessel with the block copolymer in a manner identical to that of Example 13. The results are shown in Table 2.

Example 21

Coating of Substrate

A coated tube and coated connectors were produced using the block copolymer produced in Example 11 in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition, "Elasticity Measurement of Coagulated Blood", and "Platelet Activity Measurement" were also carried out by coating a measurement vessel with the block copolymer in a manner identical to that of Example 13. The results are shown in Table 2.

Example 22

Coating of Substrate

A coated tube and coated connectors were produced using the block copolymer produced in Example 12 in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above, "Adsorption Properties Test of Protein in Blood", "Blood Perfusion Test", and "Blood Cell Counting Test" were carried out in a manner identical to that of Example 13. In addition, "Elasticity Measurement of Coagulated Blood", and "Platelet Activity Measurement" were also carried out by coating a measurement vessel with the block copolymer in a manner identical to that of Example 13. The results are shown in Table 2.

Comparative Example 1

Synthesis of Random Copolymer

After bubbling 2.92 g of 2-methoxyethyl acrylate (Toagosei Co. Ltd.) as a monomer (a), 6.66 g of N,N-dimethyl acrylamide (KOHJIN Holdings Co., Ltd.) as a monomer (b), and 0.0007 g of 2,2'-azobisisobutyronitrile, and 10 mL of 1,4-dioxane with nitrogen, the mixture was stirred at 70° C., for 24 hours, and a random polymer of the monomers (a) and (b) was produced. Moreover, the molar ratio ((a):(b)) between the monomer (a) and the monomer (b) was 500:1, 500. After the completion of the reaction, the reaction solution was added to diethyl ether. After washing with diethyl ether three times, the reaction product was dried under vacuum, and thereby an AB random copolymer having a molar ratio ((a):(b)) between the monomers (a) and (b) of 500:1,500 was produced.

[Identification of Polymer]

Similar to Example 1, the $^1$H-NMR spectrum was measured. As a result of the measurement, it was confirmed that the conversion ratio of the monomers (a) and (b) was 100% and 99.5%, respectively. It was confirmed that an AB random copolymer having a structure which corresponds to the monomer composition (molar ratio ((a):(b))=500:1500) was produced.

[Preparation of Coating Film Containing Random Copolymer]

Similar to Example 1, a coated petri dish 1' was obtained using the random copolymer obtained. When the coated petri dish 1' was visually observed, it was confirmed that the coated petri dish had similar transparency to that of the petri dish before coating.

[Protein Adsorption Properties Test]

Similar to Example 1, the protein adsorption properties test was carried out using the coated petri dish 2. As a result, the amount of the protein adsorbed (absorbance) was 0.550.

[Cell Adhesion Test]

Similar to Example 1, the cell adhesion test was carried out by cultivating normal human dermal fibroblasts using the coated petri dish 1'. As a result, it was confirmed that a considerable number of cells were adhered to the petri dish on the same level of the non-coated petri dish.

[Coating of Substrate]

A coated tube and coated connectors were produced using the random copolymer produced above in a manner identical to that of Example 13. When the coated tube and coated connectors were observed visually or using a microscope, it was confirmed that the coating was uniform and had high transparency.

[Evaluation of Antithrombotic Properties]

Using the coated tube and coated connectors which were produced above. "Adsorption Properties Test of Protein in Blood", "Blood Perfusion Test", and "Blood Cell Counting Test" were carried out in a manner identical to that of Example 13. In addition. "Elasticity Measurement of Coagulated Blood", and "Platelet Activity Measurement" were also carried out by coating a measurement vessel with the random copolymer in a manner identical to that of Example 13. Moreover, the blood after perfusion was coagulated in "Blood Perfusion Test", and it was impossible to carry out "Blood Cell Counting Test". The results are shown in Table 2.

According to the results of Comparative Example, it was found that the AB random copolymer had high protein adsorption properties, and the adhesion properties of the cells to the coating were also high.

Comparative Example 2

Protein Adsorption Properties Test

Similar to Example 1, the protein adsorption properties test was carried out at room temperature using a non-coated petri dish made of polystyrene having a diameter of 35 mm. As a result, the amount of the protein adsorbed (absorbance) was 0.624.

Comparative Example 3

Protein Adsorption Properties Test

Similar to Example 1, the protein adsorption properties test was carried out using a non-coated 15-mL precipitation tube for centrifugal separation made of polypropylene. As a result, the amount of the protein adsorbed (absorbance) was 1.375.

Comparative Example 4

Evaluation of Antithrombotic Properties

Using a non-coated tube made of polyvinyl chloride having a diameter of ⅜ inches (MERA exceline: Senko Medical Instrument Mfg. Co., Ltd.), "Adsorption Properties Test of Protein in Blood", "Blood Perfusion Test", and "Blood Cell Counting Test" were carried out. Moreover, the blood after perfusion was coagulated in "Blood Perfusion Test", and it was impossible to carry out "Blood Cell Counting Test". The results are shown in Table 2.

The results of the Protein Adsorption Properties Test in Examples and Comparative Examples are shown below.

TABLE 1

| | Block Type | Polymerization degree of Polymer (A) | Polymerization degree of Polymer (B) | Amount of Protein Adsorbed (Absorbance) |
|---|---|---|---|---|
| Example 1 | A-B | 250 | 1,440 | 0.157 |
| Example 2 | A-B-A | 250 | 1,480 | 0.044 |
| Example 3 | A-B-A | 250 | 1,490 | 0.048 |
| Example 4 | A-B-A | 200 | 1,580 | 0.046 |
| Example 5 | A-B-A | 500 | 4,840 | 0.069 |
| Example 6 | A-B-A | 230 | 1,420 | 0.058 |
| Example 7 | A-B-A | 250 | 1,410 | 0.090 |
| Example 8 | [B-A]$_4$ multibranched | 250 | 740 | 0.056 |
| Example 9 | [B-A]$_4$ multibranched | 190 | 790 | 0.060 |
| Example 10 | A-B-A | 250 | 1,490 | 0.102 |
| Example 11 | A-B-A | 250 | 13,940 | 0.320 |
| Example 12 | A-B-A | 250 | 48 | 0.310 |
| Comparative Example 1 | AB random | 500 (Monomer ratio) | 1,470 (Monomer ratio) | 0.550 |

TABLE 1-continued

|  | Block Type | Polymerization degree of Polymer (A) | Polymerization degree of Polymer (B) | Amount of Protein Adsorbed (Absorbance) |
|---|---|---|---|---|
| Comparative Example 2 | Non-coated petri dish made of polystyrene | | | 0.624 |
| Comparative Example 3 | Non-coated precipitation tube for centrifugal separation made of polypropylene | | | 1.375 |

TABLE 2

| (Unit) | Block Type | Monomer (b) | Molar ratio | BCA µg/cm² | Blood Perfusion — | SEM — | Amount of Platelet ×10³/µL | Elasticity of Blood mm | Platelet Activity U |
|---|---|---|---|---|---|---|---|---|---|
| Example 13 | A-B-A | DMAA | 250-1,480-250 | 7.5 | ◉ | ◉ | 550 | 7 | 20 |
| Example 14 | A-B-A | DMAA | 500-4,840-500 | 7.5 | ○ | ○ | 520 | 11 | 35 |
| Example 15 | A-B*-A | DMAA | 250-1,490-250 | 7.6 | ○ | ○ | 540 | 13 | 55 |
| Example 16 | A-B*-A | DMAA | 172-1,558-172 | 7.8 | ○ | ○ | 520 | 18 | 81 |
| Example 17 | (A-B)₄ | DMAA | (250-733)₄ | 8.1 | ◉ | ◉ | 520 | 10 | 30 |
| Example 18 | B*₄-4A | DMAA | (815-168)₄ | 10.6 | ○ | ○ | 480 | 18 | 64 |
| Example 19 | A-B | DMAA | 250-1,440 | 11.6 | ○ | ○ | 410 | 22 | 120 |
| Example 20 | A-B-A | ACMO | 250-1,490-250 | 6.4 | ◉ | ◉ | 520 | 10 | 26 |
| Example 21 | A-B-A | DMAA | 250-13,940-250 | 10.6 | ○ | ○ | 420 | 20 | 89 |
| Example 22 | A-B-A | DMAA | 250-48-250 | 11.6 | ○ | ○ | 410 | 25 | 123 |
| (Before Experiment) | | | | | | | 555 | | |
| Comparative Example 1 | Random | DMAA | 500:1500 | 8.9 | X | X | Unmeasurable | 61 | 250 |
| Comparative Example 2 | | | Non-coated | 18.25 | X | X | Unmeasurable | 64 | 270 |

In Blood Perfusion, ◉ means no thrombi were observed, ○ means thrombi were hardly observed, and X means a considerable number of thrombi were observed.
In SEM, ◉ means no protein was adhered, ○ means a small amount of protein was adhered, and X means a considerable amount of protein was adhered.

The invention claimed is:

1. A triblock type copolymer including a polymer (A) containing a monomer (a) represented by the general formula (1) and a polymer (B) containing a monomer (b) represented by the following formula (2):

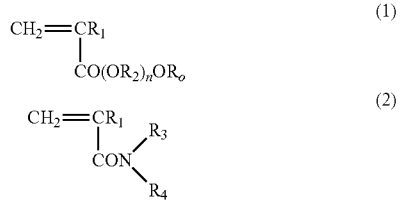

in the formulae (1) and (2), $R_O$ represents an alkyl group having 1 to 3 carbon atoms; $R_1$ represents a hydrogen atom, or a methyl group; $R_2$ represents an alkylene group having 2 or 3 carbon atoms; $R_3$, and $R_4$ represent a hydrogen atom, or an alkyl group having 1 or 2 carbon atoms; and n represents an integer from 1 to 9,
wherein the triblock type copolymer is A-B-A type or A-B*-A type; and
the copolymer B* contains the monomer (a) represented by the general formula (1) and the monomer (b) represented by the general formula (2).

2. The triblock type copolymer according to claim 1, wherein the molar ratio (A:B) between the polymer (A) and the polymer (B) is in a range from 1:50 to 50:1.

3. The triblock type copolymer according to claim 1, wherein the polymer (B*) is a copolymer including the monomers (b) and (a), and the molar ratio ((b):(a)) between the monomer (b) and the monomer (a) in the polymer (B) is in a range from 99:1 to 10:90.

4. The triblock type copolymer according to claim 1, wherein the polymerization degree of the polymer (A) is in a range from 30 to 3,000, and the polymerization degree of the polymer (B) is in a range from 20 to 20,000.

5. A coating film containing a triblock type copolymer including a polymer (A) containing a monomer (a) represented by the general formula (1) and a polymer (B) containing a monomer (b) represented by the following formula (2):

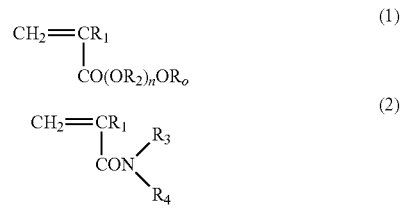

wherein in the formulae (1) and (2), $R_O$ represents an alkyl group having 1 to 3 carbon atoms; $R_1$ represents a hydrogen atom, or a methyl group; $R_2$ represents an alkylene group having 2 or 3 carbon atoms; $R_3$, and $R_4$ represent a hydrogen atom, or an alkyl group having 1 or 2 carbon atoms; and n represents an integer from 1 to 9,
wherein the triblock type copolymer is A-B-A type or A-B*-A type; and the copolymer B* contains the monomer (a) represented by the general formula (1) and the monomer (b) represented by the general formula (2).

6. A protein adsorption inhibitor using the coating film according to claim 5.

7. A cell culture substrate using the coating film according to claim 5.

8. An antithrombotic coating agent including a triblock type copolymer that includes a polymer (A) containing a monomer (a) represented by the general formula (8), and a polymer (B) containing a monomer (b) represented by the following formula (9):

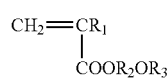

(8)

in the formula (8), $R_1$ represents a hydrogen atom or a methyl group; $R_2$ represents an alkylene group having 2 or 3 carbon atoms; and $R_3$ represents an alkyl group having 1 to 3 carbon atoms:

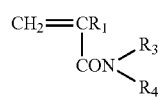

(9)

in the formula (9), $R_1$ represents a hydrogen atom, or a methyl group; $R_3$, and $R_4$, represent a hydrogen atom, or an alkyl group having 1 or 2 carbon atoms, wherein the triblock type copolymer is A-B-A type or A-B*-A type; and the copolymer B* contains the monomer (a) represented by the general formula (8) and the monomer (b) represented by the general formula (9).

9. The antithrombotic coating agent according to claim 8, wherein the polymer (A) is not dissolved in water, and the polymer (B) or the copolymer (B*) is dissolved in water.

10. The antithrombotic coating agent according to claim 8, wherein the molar ratio (monomer (b)/monomer (a)) between the monomer (b) and the monomer (a) is in a range of 99/1 to 10/90.

11. The antithrombotic coating agent according to claim 8, wherein the molar ratio (polymer (A)/polymer (B) or polymer (A)/copolymer (B*)) between the polymer (A) and the polymer (B) or the copolymer (B*) is in a range of 1:50 to 50:1.

12. The antithrombotic coating agent according to claim 8, wherein the polymerization degree of the polymer (A) is in a range of 30 to 3,000, and the polymerization degree of the polymer (B) or the copolymer (B*) is in a range of 20 to 20,000.

13. The antithrombotic coating agent according to claim 8, wherein the antithrombotic coating agent includes 0.05 to 10 parts by mass of the triblock type copolymer, and 90 to 99.95 parts by mass of a solvent containing any one of ethanol, methanol, and isopropyl alcohol as a main component.

14. A surface-modifying agent for a medical or biochemical instrument comprising the coating film according to claim 5.

15. The triblock type copolymer according to claim 2, wherein the polymer (B*) is a copolymer including the monomers (b) and (a), and the molar ratio ((b):(a)) between the monomer (b) and the monomer (a) in the polymer (B) is in a range from 99:1 to 10:90.

* * * * *